(12) United States Patent
Kim

(10) Patent No.: US 11,393,466 B2
(45) Date of Patent: Jul. 19, 2022

(54) ELECTRONIC DEVICE AND METHOD OF PROVIDING DIALOG SERVICE BASED ON ELECTRONIC MEDICAL RECORD

(71) Applicant: Samsung Electronics Co., Ltd., Gyeonggi-do (KR)

(72) Inventor: Joohyun Kim, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 210 days.

(21) Appl. No.: 16/659,877

(22) Filed: Oct. 22, 2019

(65) Prior Publication Data
US 2020/0126550 A1 Apr. 23, 2020

(30) Foreign Application Priority Data
Oct. 23, 2018 (KR) .................. 10-2018-0126808

(51) Int. Cl.
*G10L 15/22* (2006.01)
*G10L 15/18* (2013.01)
*G10L 15/30* (2013.01)
*G06F 3/16* (2006.01)
*G16H 10/60* (2018.01)
*G06N 20/00* (2019.01)

(52) U.S. Cl.
CPC .............. *G10L 15/22* (2013.01); *G06F 3/167* (2013.01); *G06N 20/00* (2019.01); *G10L 15/1815* (2013.01); *G10L 15/1822* (2013.01); *G10L 15/30* (2013.01); *G16H 10/60* (2018.01); *G10L 2015/223* (2013.01)

(58) Field of Classification Search
CPC ........ G10L 15/30; G10L 15/18–15/187; G10L 17/00–1726; G06N 20/00; G16H 10/60; G06F 3/167
See application file for complete search history.

(56) References Cited

U.S. PATENT DOCUMENTS

| | | | |
|---|---|---|---|
| 6,362,747 B1 * | 3/2002 | Parker .................. | G08B 25/008 340/5.2 |
| 6,704,394 B1 * | 3/2004 | Kambhatla ........... | H04M 3/533 379/67.1 |
| 2007/0050453 A1 * | 3/2007 | Carthern .............. | G06Q 10/107 709/206 |
| 2009/0306983 A1 | 12/2009 | Bhandari | |

(Continued)

FOREIGN PATENT DOCUMENTS

JP 2017-108767 A 6/2017

*Primary Examiner* — Abul K Azad
(74) *Attorney, Agent, or Firm* — Cha & Reiter, LLC

(57) ABSTRACT

An electronic device and method are disclosed herein. The electronic device includes a communication interface, a processor and a memory. The processor implements the method, including detecting a login to a first user account through a communication interface, identifying electronic medical record (EMR) data stored in a memory corresponding to the first user account based at least in part on a result of the detected login, generate first utterance data for output through a user device based at least in part on the stored EMR data, wherein the first utterance data is generated before any data associated with utterance is received from the user device; and transmitting the generated first utterance data to the user device through the communication interface for output by the user device.

17 Claims, 16 Drawing Sheets

(56) References Cited

U.S. PATENT DOCUMENTS

| | | |
|---|---|---|
| 2012/0253801 A1* | 10/2012 | Santos-Lang ........... G10L 15/22 704/235 |
| 2013/0045685 A1* | 2/2013 | Kiani ..................... G08B 21/24 455/41.2 |
| 2015/0142704 A1 | 5/2015 | London |
| 2016/0042483 A1* | 2/2016 | Vo .......................... G16H 10/60 705/3 |
| 2017/0169203 A1 | 6/2017 | Onodera |
| 2017/0185375 A1* | 6/2017 | Martel .................. G06F 40/279 |
| 2017/0293845 A1* | 10/2017 | McAllister .............. H04L 47/10 |
| 2018/0068082 A1 | 3/2018 | Brown et al. |
| 2019/0051379 A1* | 2/2019 | Owen ................. G06K 9/00288 |
| 2019/0069145 A1* | 2/2019 | Dantsker ............. G08B 25/016 |

\* cited by examiner

ELECTRONIC DEVICE AND METHOD OF PROVIDING DIALOG SERVICE BASED ON ELECTRONIC MEDICAL RECORD

CROSS-REFERENCE TO RELATED APPLICATION(S)

This application is based on and claims priority under 35 U.S.C. 119 to Korean Patent Application No. 10-2018-0126808, filed on Oct. 23, 2018, in the Korean Intellectual Property Office, the disclosure of which is herein incorporated by reference in its entirety.

BACKGROUND

Technical Field

Certain embodiments of the disclosure relate to electronic devices providing a dialog service, and more specifically, to electronic devices providing a natural language dialog services to medical consumers based on application of machine-learning to electronic medical records (EMRs).

Description of Related Art

There is now wide use of electronic devices that are capable of provide a "dialog" service (e.g., a machine-implemented conversational interaction, often using 'Natural Language Processing' or NLP) based on machine learning. Electronic devices which provide a dialog service may use a recognition model formed by machine learning to understand and/or extract commands and other interaction from a user's utterance. Electronic devices which provide a dialog service may generate an answer related to the user's utterance, in response to the user's utterance. Electronic devices which provide a dialog service may interpret the user's utterance using machine learning, and execute a particular operation related to the user's utterance. Electronic devices which provide a dialog service may execute particular applications, open file, send messages, execute purchases based on user-utterances interpreted as commands.

Conventional dialog services interpret the user's utterance, extract an estimated meaning of the user's request, output a response matching the user's request, and/or perform a particular operation requested by the user. In some cases, the topic or context of a user utterance in the form of dialog is determined depending on the user's request. Since the user issues an utterance and the dialog topic is determined depending on the user's inputs, it may be difficult for the dialog service provider to specify a topic and facilitate user interaction using the dialog.

In conventional dialog services, since the user's request is atopical, the dialog service-provider electronic device may be required to define various predefined topics, and "learn" a number of preset dialog options related to the topics, in order to interpret and execute functions based on user utterances related to various topics. Accordingly, when a learned dialog regards a plurality of different topics, a successful dialog recognition rate for the electronic device may be lowered.

Medical information services may include the user's personal information which requires a measure of confidentiality, to prevent leakage of the user's personal information to others.

The above information is presented as background information only to assist with an understanding of the disclosure. No determination has been made, and no assertion is made, as to whether any of the above might be applicable as prior art with regard to the disclosure.

SUMMARY

According to certain embodiments, in an electronic device and a method performed on the electronic device, the electronic device may start a dialog earlier than the user and take the lead in determining the topic of dialog. According to certain embodiments, the electronic device may use a recognition model created by learning scope-limited data. According to certain embodiments, the electronic device may perform a user authentication process to identify whether the user currently using a dialog service is the same figure as the one specified by the user account.

In accordance with certain embodiments, a server configured to provide a dialog service includes a communication interface configured to communicate with at least one user device, at least one processor operatively connected with the communication interface, and a memory operatively connected with the processor and configured to store electronic medical record (EMR) data, wherein the memory stores instructions that, when executed, cause the at least one processor to: detect a login to a first user account through the communication interface, identify stored EMR data that corresponds to the first user account based at least in part on a result of the detected login, generate first utterance data for output through the user device based at least in part on the identified stored EMR data, wherein the first utterance data is generated before any voice commands are received from the user device, and transmit the generated first utterance data to the user device through the communication interface for output by the user device.

In accordance with certain embodiments, a method of operating a server configured to provide a dialog service detecting a login to a first user account through a communication interface, identifying electronic medical record (EMR) data stored in a memory corresponding to the first user account based at least in part on a result of the detected login, generate first utterance data for output through a user device based at least in part on the stored EMR data, wherein the first utterance data is generated before any voice commands are received from the user device, and transmitting the generated first utterance data to the user device through the communication interface for output by the user device.

In accordance with certain embodiments, an electronic device includes a housing, a touchscreen display exposed through a first portion of the housing, a communication interface disposed inside the housing and configured to communicate with an external electronic device, a voice input/output device disposed in a second portion and/or a third portion of the housing and configured to receive and output utterance data, at least one processor positioned disposed the housing and operatively coupled with the touchscreen display, the communication interface, and the voice input/output device, and a memory disposed inside the housing and operatively coupled with the processor, wherein the memory stores instructions executable to cause the at least one processor to: transmit a login request associated with a first user account using the communication interface to the external electronic device, receive, through the communication interface, a first utterance data generated by the external electronic device based at least in part on electronic medical record (EMR) data stored in association with the first user account based at least in part on a result of the login request, output at least one of a sound and a display image based on the first utterance data through at least one of the voice input/output device and the touchscreen display, and receive, using the voice input/output device, a response to at least one of the sound and display image. Other aspects, advantages, and salient features of the disclosure will become apparent to those skilled in the art from the following detailed description, which, taken in conjunction with the annexed drawings, discloses example embodiments of the disclosure.

BRIEF DESCRIPTION OF THE DRAWINGS

A more complete appreciation of the disclosure and many of the attendant aspects thereof will be readily obtained as the same becomes better understood by reference to the following detailed description when considered in connection with the accompanying drawings, in which.

The same or similar reference denotations may be used to refer to the same or similar elements throughout the specification and the drawings.

DETAILED DESCRIPTION

Figure 1:
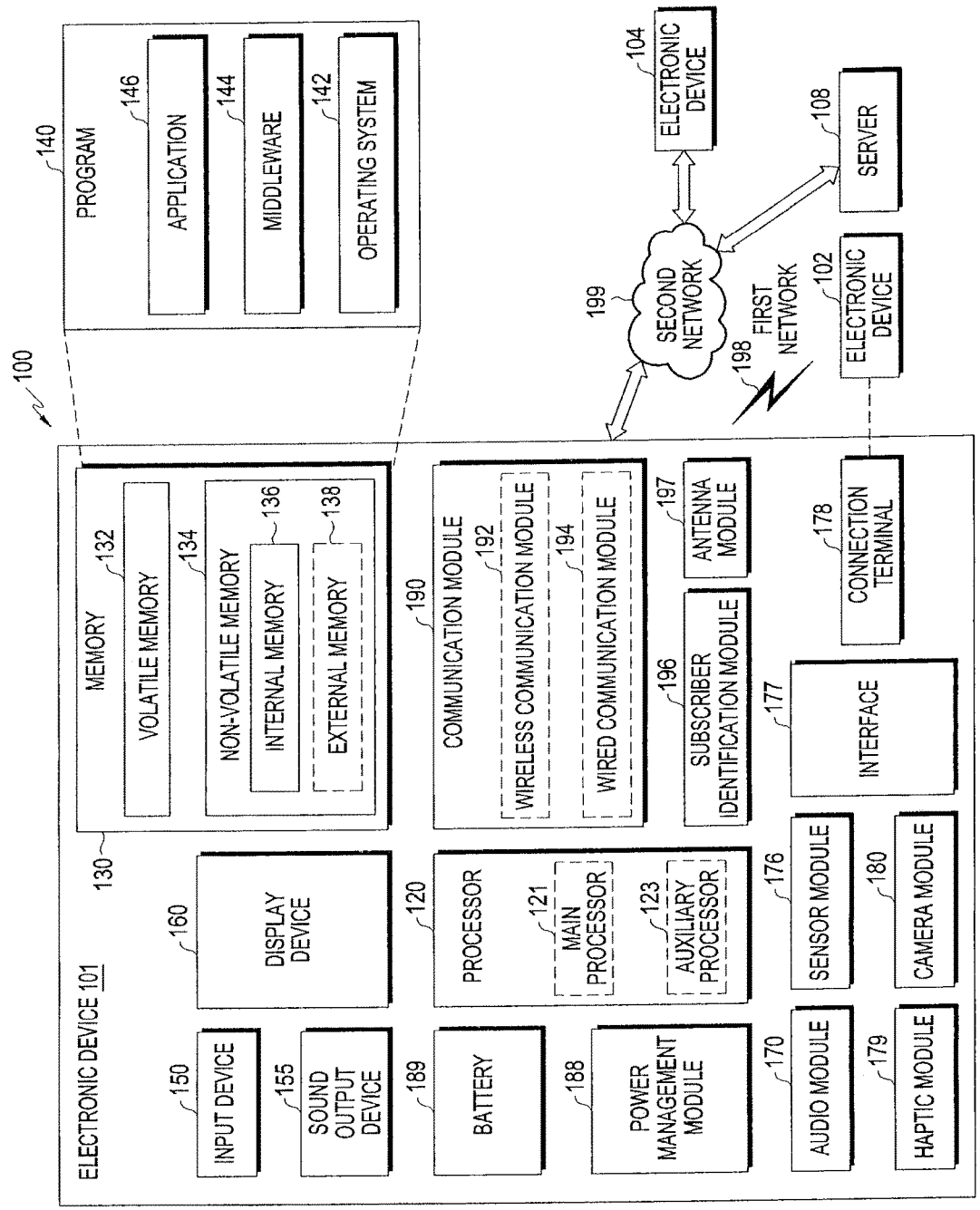
FIG. 1 is a block diagram illustrating an electronic device in a network environment according to an example embodiment.

FIG. 1 is a block diagram illustrating an electronic device 101 in a network environment 100 according to certain embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to an embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing a recording, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 1801, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or motion) or electrical stimulus which may be recognized by a user via his or her tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 388 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device). According to an embodiment, the antenna module may include one antenna including a radiator formed of a conductor or conductive pattern formed on a substrate (e.g., a printed circuit board (PCB)). According to an embodiment, the antenna module 197 may include a plurality of antennas. In this case, at least one antenna appropriate for a communication scheme used in a communication network, such as the first network 198 or the second network 199, may be selected from the plurality of antennas by, e.g., the communication module 190. The signal or the power may then be transmitted or received between the communication module 190 and the external electronic device via the selected at least one antenna. According to an embodiment, other parts (e.g., radio frequency integrated circuit (RFIC)) than the radiator may be further formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, instructions or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
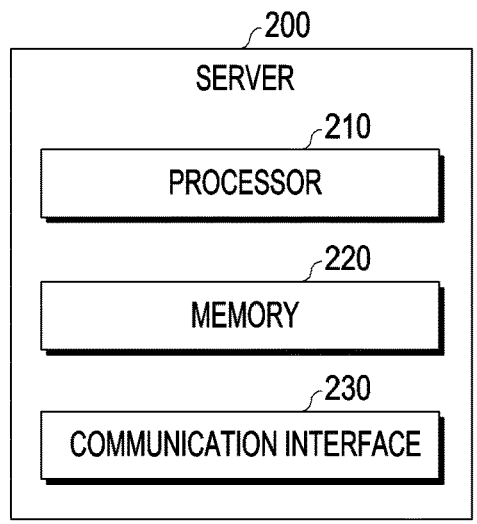
FIG. 2 is a view illustrating a structure of a server according to an example embodiment.

FIG. 2 is a view illustrating a structure of a server 200 according to an embodiment. The server 200 of FIG. 2 may be a server 108 which may communicate with the electronic device 101 of FIG. 1 via a second network 199. According to an embodiment, the server 200 may include a processor 210, a memory 220, and a communication interface 230. The processor 210 may execute, for example, software to control at least one other component (e.g., a hardware or software component) of the server 200 coupled with the processor 210, and may perform various data processing or computation. According to an embodiment, as at least part of the data processing or computation, the processor 210 may load a command or data received from another component (e.g., the memory 220 or communication interface 230) onto a volatile memory, process the command or the data stored in the volatile memory, and store resulting data in a non-volatile memory. The memory 220 may store various data used by at least one component (e.g., the processor 210 or the communication interface 230) of the server 200. The various data may include, for example, software and input data or output data for a command related thereto. The memory 220 may include a volatile memory or a non-volatile memory. The communication interface 230 may support establishing a direct (e.g., wired) communication channel or a wireless communication channel between the server 200 and the external electronic device (e.g., the electronic device 101 or another server (not shown)) and performing communication via the established communication channel.

Figure 3:
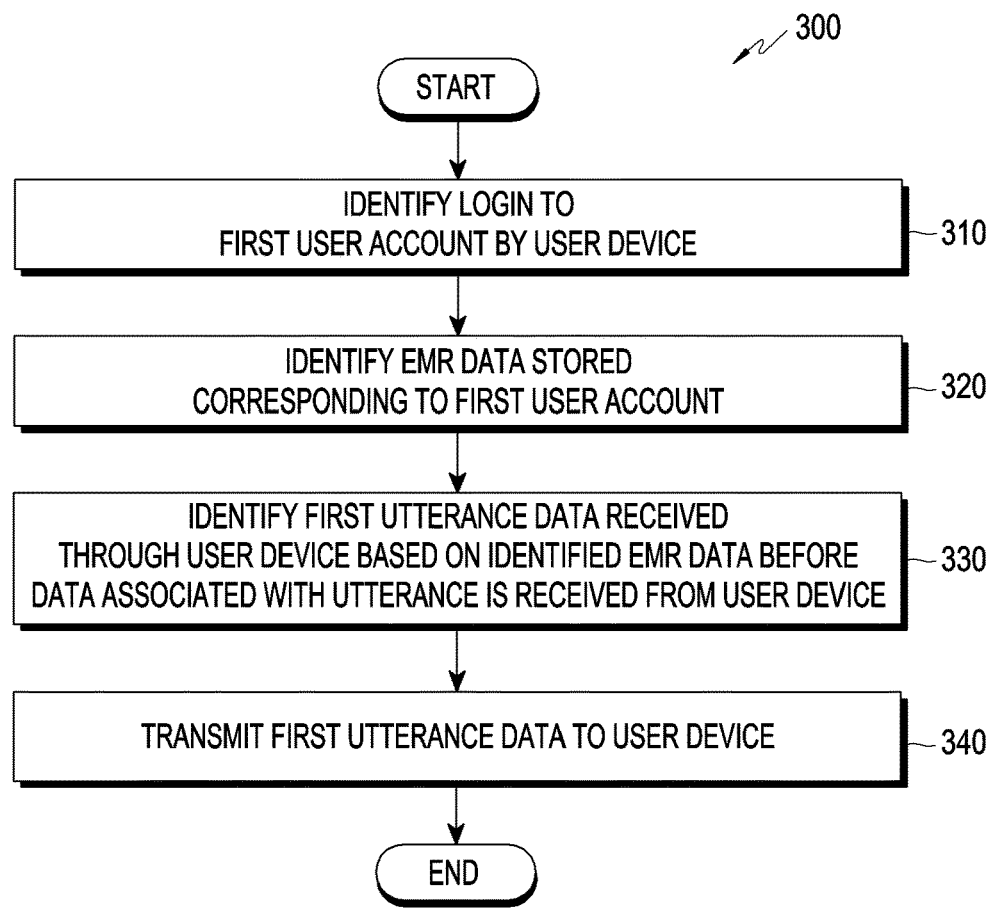
FIG. 3 is a flowchart illustrating operations of a server according to an example embodiment.

FIG. 3 is a flowchart illustrating an operation 300 of a server to provide a dialog service (e.g., a NLP dialog/conversational interaction with the user) according to an embodiment. According to an embodiment, in operation 310, the server 200 may identify that a login to a first user account has been performed by a user device (e.g., the electronic device 101) using the communication interface 230. The first user account may be associated with the server 200 to provide, e.g., a dialog service. For example, the server 200 to provide a dialog service may be operated by an organization to provide dialog services, and the first user account may be an account created through the organization operating the server 200. In this case, the server 200 may receive information for login via a network (e.g., the second network 199) from the user device and identify that login has been performed based on information received from the user device. According to an embodiment, the first user account may be an account associated with an organization other than a medical organization to provide communication services (e.g., messaging, e-mail or other forms of electronic dialog). For example, the first user account may be an account created via, e.g., service providers (e.g., Google, Facebook, Kakao, Naver, Tencent, Baidu, etc.). In this case, the server 200 may identify that login to the first user account has been performed based on information received from service providers via the Internet or a computer network (e.g., local area network (LAN) or wide area network (WAN) or such a long-range communication network).

As used herein, "server 200 may perform a particular operation" may be appreciated as the processor 210 performing the particular operation. As used herein, "server 200 performs a particular operation" may also be appreciated as the processor 210 controlling hardware in the server 200 or hardware outside the server 200 to perform the particular operation. Further, "server 200 performs a particular operation" may be appreciated as the memory 220 storing instructions enabling at least one of the processor 210 or hardware to perform the particular operation.

In operation 320, the server 200 may identify first EMR data stored in the memory 220 corresponding to the first user account based on at least part of the result of login. The first EMR data may be data obtained based on an EMR. The first EMR data stored corresponding to the first user account may be data obtained based on a user's EMR corresponding to the first user account. According to an embodiment, the EMR may be created in a format defined by, e.g., Health Level 7 (HL7) standards. The process of obtaining the first EMR data from the EMR is described below in detail with reference to FIGS. 8 to 10. As described below, the process of obtaining the first EMR data from the EMR according to an embodiment may be performed by the server 200 and the first EMR data may be stored in the memory 220. Alternatively, the process of obtaining the first EMR data from the EMR may be performed by an external device (e.g., a separate server) other than the server 200, the obtained first EMR data may be stored in the external device, and the server 200, after identifying login to the first user account, may identify the first EMR data stored in the external device corresponding to the first user account from the external device via a network.

In operation 330, prior to receive any data indicating vocal commands from the user device, the server 200 may identify and/or generate a vocal query (e.g., a "first utterance data") that is relevant or otherwise based on the identified EMR data for the first user account. For example, the first EMR data identified as corresponding to the first user account may include the user's medical information, and the generated vocal prompt based on the identified first EMR data may include a query related to the user's medical information. For example, the first EMR data may indicate a prescribed medication for the user, and the generated vocal prompt may query whether the prescribed medication is being regularly consumed. According to an embodiment, the first utterance data may be output to the user in an audio format by the user device (e.g., user a speaker), or may be output to the user using a combination of voice and text.

The retrieval (or generation) of the vocal prompt (e.g., the first utterance data) may occur before the data associated with any utterance is received from the user device. In other words, the server 200 identifies the first utterance data before the user enters a voice command (e.g., an utterance via the user device). Thus, in the NLP dialog between the dialog service provider, i.e., the server 200, and the user, the server 200 may transmit a text message or audio for output through the user device to initiate NLP dialog with the user. A method for the dialog service provider to start a dialog earlier than the user is described below with reference to FIGS. 11 to 13. Since the topic of the dialog is determined by the dialog service provider of the user and the dialog service provider, a recognition model limited depending on the topic determined when understanding the user's utterance may be used and, thus, the recognition rate of the user's utterance may be increased. Further, since the server 200 starts a dialog earlier than the user, it may be easy for the server 200 to lead the user to complete a particular task.

In operation 340, the server 200 may transmit the generated vocal prompt (e.g., first utterance data) to the user device (e.g., the electronic device 101) using the communication interface 230. According to an embodiment, the generated vocal prompt may be data which has not undergone natural language generation (NLG). According to another embodiment, the first utterance data may indicate a text-type natural language obtained via natural language generation. According to another embodiment, the first utterance data may indicate a voice signal obtained by performing a text-to-speech process on a text-type natural language. It will be apparent to one of ordinary skill in the art that the utterance data (e.g., the third utterance data described below with reference to FIG. 5) described herein as transmitted from the server 200 to the user device may be data which has not undergone natural language generation (NLG), data indicating a text-type natural language, or data indicating a voice signal. The utterance data (e.g., the second utterance data described below with reference to FIGS. 5 and 6 or the fourth utterance data described below with reference to FIGS. 14, 16, 18, and 19) described herein as received by the server 200 from the user device may be data indicating a voice signal, data indicating a text-type natural language obtained by performing a speech-to-text (STT) process on a voice signal, or data obtained by performing a natural language understanding (NLU) on a text-type natural language.

As the server 200 performs operation 340, the user device may receive the first utterance data from the server 200, and the user device may output a voice corresponding to the first utterance data through a voice input/output device (e.g., the sound output device 155). According to an embodiment, the user device may output a text corresponding to the first utterance data through a display (e.g., the display device 160). The user device may receive, from the user, the user's response to the voice and/or text-type utterance output to the user.

Figure 4:
FIG. 4 is a view illustrating a screen displayed on a user device where a dialog service is provided according to an example embodiment.

FIG. 4 illustrates a screen displayed on a user device (e.g., the electronic device 101) when a dialog service is provided according to an embodiment. According to an embodiment, when a dialog service is provided, a service screen 400 may be displayed on the display (e.g., the display device 160) of the user device. The service screen 400 may be a screen provided after a dialog service provider application is logged into a dialog service provider. According to an embodiment, a dialog display area 410 may be displayed as at least part of the service screen 400. According to an embodiment, a text 420 corresponding to utterance data (e.g., the generated vocal prompt or "first utterance data" described with reference to FIG. 3 or the third utterance data described with reference to FIG. 5) transmitted from the server (e.g., the server 200) to the user device may be displayed on the dialog display area 410. Further, a text 430 (e.g., the second utterance data described with reference to FIGS. 5 and 6 or the fourth utterance data described with reference to FIGS. 14, 16, 18, and 19) corresponding to the utterance data received from the user device by the server 200 may be displayed on the dialog display area 410. According to an embodiment, the text 420 corresponding to the utterance data transmitted from the server 200 to the user device may be displayed on the left side of the dialog display area 410. In this case, the text 430 corresponding to the utterance data received from the user device by the server 200 may be displayed on the right side of the dialog display area 410. Although FIG. 4 illustrates an example in which the dialog display area 410 is present, such an embodiment is also possible where there is no dialog display area 410, no text corresponding to the utterance data is output, and an utterance is entered and output in the form of a voice via the user device's voice input/output device (e.g., the sound output device 155 and the input device 150).

According to an embodiment, at the user's turn of utterance, a first image 440 may be displayed on the service screen 400. According to an embodiment, the first image 440 may be an image representing a microphone. According to an embodiment, at the server (200)'s turn of utterance, the first image 440 may not be displayed in the position of the first image 440 or the first image 440 may be displayed in a different size, shape, or color than when the user issues a utterance. According to an embodiment, a second image 450 may be displayed on the service screen 400. According to an embodiment, at the utterance turn of the server 200 which is the dialog service provider, the second image 450 may be an image representing a speaker. According to an embodiment, at the user's turn of utterance, the second image 450 may not be displayed or may be displayed in a different size, shape, or color than when the server 200 issues an utterance. According to an embodiment, the first image 440 may be positioned on the right side of the service screen 400, and the second image 450 may be positioned on the left side of the service screen 400. As set forth above, when the first utterance data is received from the server 200, the electronic device 101 may display the text 420 corresponding to the first utterance data. Since the server 200 may transmit the first utterance data before receiving the utterance from the user, the text 420 corresponding to the first utterance data received from the server 200 may first be displayed on the dialog display area 410.

Figure 5:
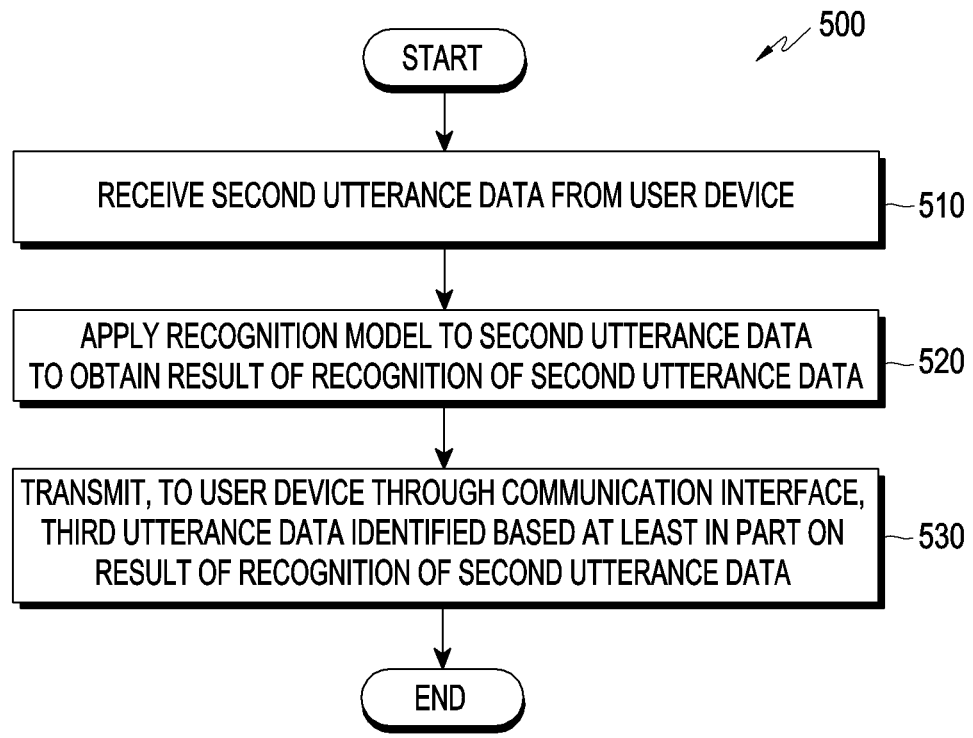
FIG. 5 is a flowchart illustrating operations of a server according to an example embodiment.

FIG. 5 is a flowchart illustrating an example operation 500 performed by a server to recognize a user utterance according to an embodiment. In operation 510, a server (e.g., the server 200) may receive second utterance data from a user device (e.g., the electronic device 101), such as a vocal command or request from the user, as received by the user device. After being transmitted to the server 200, in operation 520, the server 200 may execute algorithmic recognition of the second utterance data by applying a recognition model to the received second utterance data. The recognition model may be created by EMR machine learning which is described below. The creation of the recognition model may be performed by the server 200 or by an external device (e.g., a separate server) other than the server 200. The EMR data which is target for learning may include EMR data which is based on the user's EMR and EMR data which is based on one or more other users' EMR.

Subsequently, in operation 530, the server 200 may transmit third utterance data identified, retrieved or otherwise generated based at least in part on the result of the algorithmic recognition executed on the second utterance data. The third utterance data may be transmitted through a communication interface (e.g., the communication interface 230) to the user device. For example, when executing recognition on the second utterance data indicates that the user's blood pressure is 100, the third utterance data may include a message stating the recognized blood pressure is too low, and that the user's primary care doctor will contact the user. In this case, the server 200 may transmit information about the third utterance data to another electronic device (e.g., the electronic device 104 of FIG. 1), such as the electronic device 104 which may correspond to the user's primary care doctor. Further, the server 200 may transmit a request for the primary care doctor to contact the user utilizing contact information stored in association with the first user account (e.g., contact information indicated to the electronic device 101 or contact information about the caregiver of the first user account).

Figure 6:
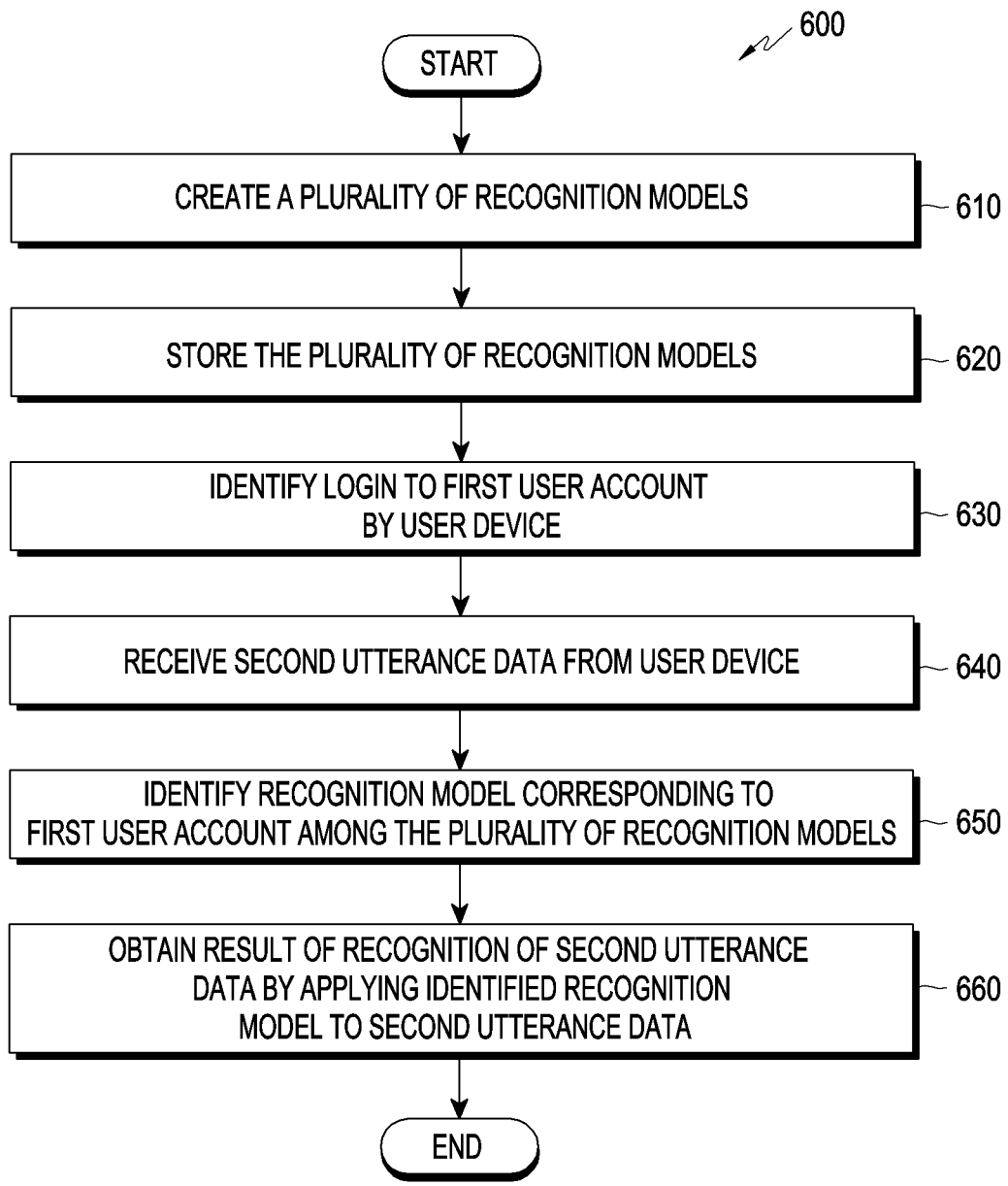
FIG. 6 is a flowchart illustrating operations of a server according to an example embodiment.

FIG. 6 is a flowchart illustrating an example operation 600 of a server according to an embodiment. In operation 610, a server (e.g., the server 200) may create (or obtain) a plurality of recognition models. The plurality of recognition models may be generated (or obtained) by learning EMR data divided as per user groups or disease names. For example, user groups may be divided with respect to the medical organization to which the patient's primary care doctor belongs. As another example, the user groups may be defined according to medical departments, such as cardiology, pulmonology, and gastroenterology in which case a recognition model corresponding to each medical department may be created by learning EMR data obtained from the patients' EMRs divided with respect to the medical departments. As another example, the user groups may be defined with respect to at least one of the user's domicile, age, and family in which case corresponding recognition models may be created by learning EMR data obtained from the patients' EMRs divided with respect to at least one of domicile, age, and family. In another example, a recognition model corresponding to each disease name may be created by learning EMR data divided according to disease names. Although FIG. 6 illustrates that a plurality of recognition models are created by the server 200, a plurality of recognition models may be created by an external electronic device (e.g., a separate server) other than the server 200 in another embodiment.

In operation 620, the server 200 may store the plurality of recognition models that were generated. According to an embodiment, when the plurality of recognition models are generated by an external electronic device other than the server 200, the plurality of recognition models may be transmitted from the external electronic device to the server 200 via a network and may then be stored in the memory 220 of the server 200. When the plurality of recognition models is generated by an external electronic device other than the server 200, the server 200 may update the plurality of recognition models stored by communication with the external electronic device. For example, the update of the recognition models may be performed periodically as per predetermined cycles. As another embodiment, the update of the recognition model may be triggered by the external electronic device or as the server 200 identifies login by the user device (e.g., the electronic device 101). According to an embodiment, the plurality of recognition models may be stored in the user device (e.g., the electronic device 101). In this case, operations 510 and 520 of FIG. 5 may be replaced with the operations of obtaining the result of recognition of an utterance by applying the recognition model to the second utterance data by the user device and receiving the result of recognition of the second utterance data from the user device by the server 200 to thereby obtain the result of recognition of the second utterance data. When the plurality of recognition models is stored in the user device, the user device may update the plurality of recognition models stored by communication with the server 200. For example, the update of the recognition models may be performed periodically as per predetermined cycles. As another example, the update of recognition model may be triggered by the external electronic device or the server 200 or may be triggered as the server 200 identifies login by the user device.

In operation 630, the server 200 may identify that login to the first user account has been performed by the user device. Details of operation 630 have been described above in connection with operation 310 of FIG. 3. Accordingly, a further description of this operation will be omitted in the interests of brevity.

In operation 640, the server 200 may receive second utterance data from the user device. Details of operation 640 have been described above in connection with operation 510 of FIG. 5. Accordingly, a further description of this operation will be omitted in the interests of brevity.

In operation 650, the server 200 may identify the recognition model corresponding to the first user account among the stored plurality of recognition models. For example, the plurality of recognition models may be stored with reference to medical departments to which each pertains, such as cardiology, pulmonology, and gastroenterology. When the user corresponding to the first user account is known to be in cardiology-related treatment, the recognition model corresponding to cardiology may be selected, identified or preferentially utilized. According to an embodiment, when the user corresponding to the first user account corresponds to one or more of a plurality of recognition models, the corresponding plurality of recognition models may be identified.

In operation 660, the server 200 may obtain the result of recognition of the second utterance data by applying the identified recognition model to the second utterance data. According to an embodiment, when the user corresponding to the first user account corresponds to a plurality of recognition models, the result of recognition of the second utterance data may be obtained by applying the matching model or models from among the plurality of recognition models.

According to an embodiment, when the plurality of recognition models is stored in the user device, operations 630 to 660 may be replaced with the operations of receiving, by the user device, information indicating that login to the first user account has succeeded from the server 200, receiving, by the user device, the user's utterance through a voice input/output device (e.g., the input device 150) to identify the second utterance data, identifying, by the user device, the recognition model corresponding to the first user account among the plurality of recognition models, obtaining, by the user device, the result of recognition of the second utterance data by applying the identified recognition model to the second utterance data, transmitting, by the user device, the result of recognition of the second utterance data to the server 200, and receiving, by the server 200, the result of recognition of the second utterance data from the user device.

Figure 7:
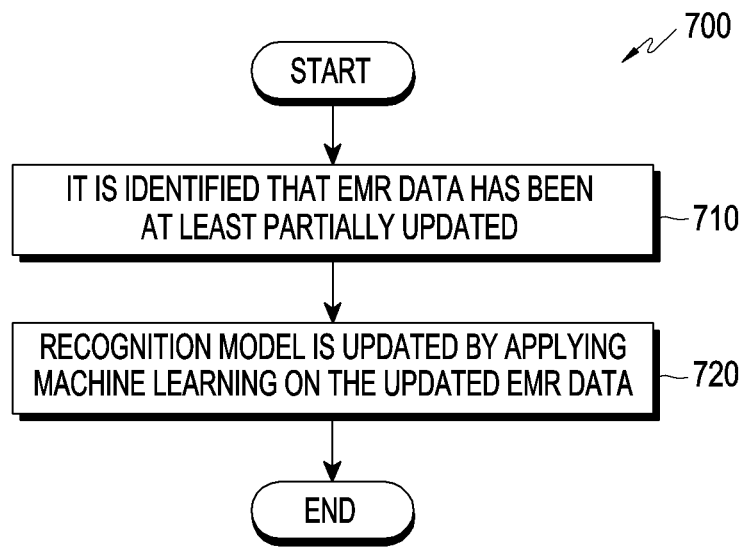
FIG. 7 is a flowchart illustrating a method of updating a recognition model according to an example embodiment.

FIG. 7 is a flowchart illustrating an example method 700 of updating a recognition model according to an embodiment. In operation 710, it may be detected that EMR data has been at least partially updated. According to an embodiment, when the creation of a recognition model is performed by the server 200, operation 710 may be performed by the server 200. According to an embodiment, when the creation of the recognition model is performed by an external electronic device (e.g., a separate server) other than the server 200, operation 710 may be performed by the external electronic device. The update of EMR data may occur as the EMR itself updates. The update of EMR data or the update of EMR may encompass changes in the content of existing EMR data or existing EMR, creation of new EMR data or adding of new content to the EMR, deletion of existing EMR data or the whole or part of EMR. For example, when a patient's medical team changes a prescription for the patient, a change may be made to the medication entries in the patient's EMR, and the existing EMR data related to the patient's medication may be altered. As another example, when the patient opts to reject using of an external dialog service provider (e.g., Google, Facebook, Kakao, Naver, Tencent, or Baidu), or to delete his or her account by canceling a corresponding membership, the EMR data related to the patient may be deleted. According to an embodiment, when the treatment on the patient is terminated, the EMR data related to the patient may be deleted. According to an embodiment, when the treatment on the patient stops, the EMR data related to the patient may be deleted.

In operation 720, the recognition model may be updated by executing machine learning on the updated EMR data. According to an embodiment, when the creation of a recognition model is performed by the server 200, operation 720 may be performed by the server 200. According to an embodiment, when the creation of the recognition model is performed by an external electronic device (e.g., a separate server) other than the server 200, operation 720 may be performed by the external electronic device.

Figure 8:
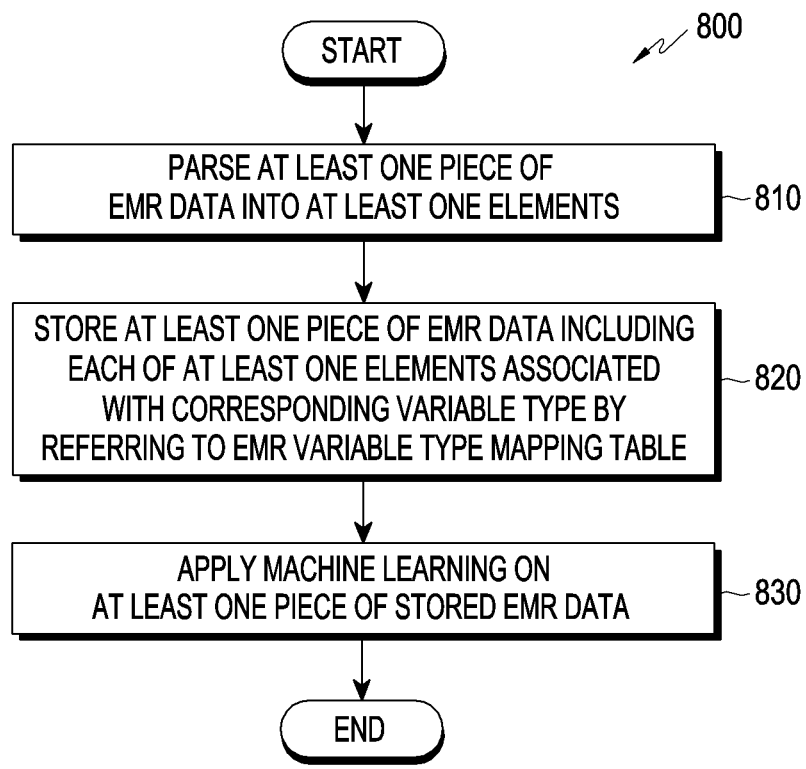
FIG. 8 is a flowchart illustrating a method of learning EMR data from an EMR according to an example embodiment.
Figure 9:
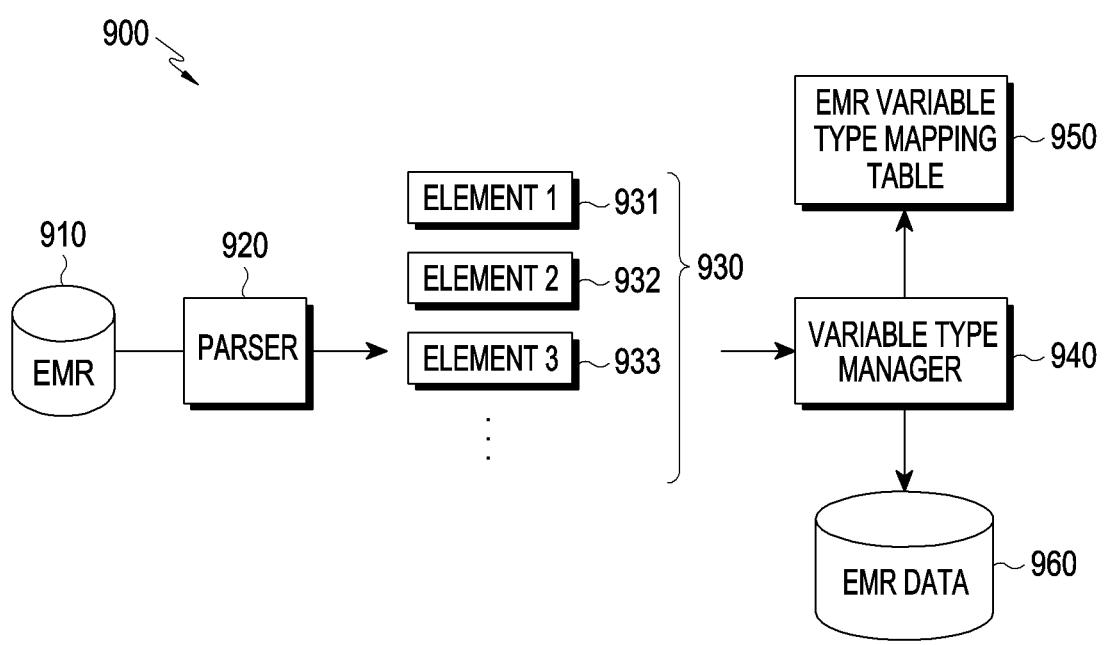
FIG. 9 is a view illustrating a process of learning EMR data from an EMR according to an example embodiment.
Figure 10:
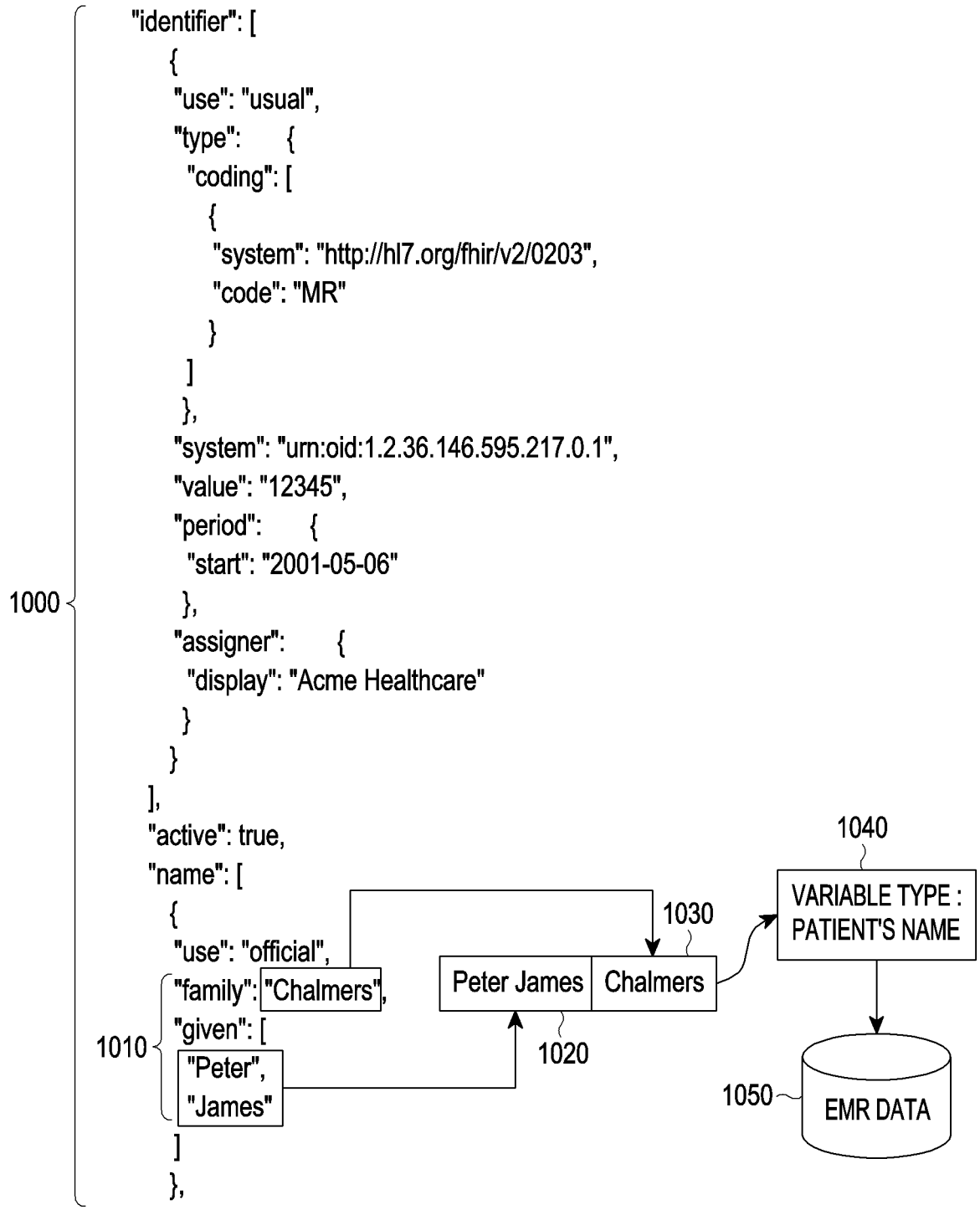
FIG. 10 is a view illustrating an example process of learning EMR data from an EMR according to an example embodiment.

FIG. 8 is a flowchart illustrating an example method 800 of learning EMR data from an EMR according to an embodiment. FIG. 9 is a view illustrating an example process 900 of learning EMR data from an EMR according to an embodiment. FIG. 10 is a view illustrating an example process of learning EMR data from an EMR according to an embodiment.

Although each operation of the method 800 of FIG. 8 is described below to be performed by the server 200, when the creation of the recognition model is performed by an external electronic device (e.g., a separate server) other than the server 200, each operation of the method 800 of FIG. 8 may be performed by the external electronic device. Although the components (e.g., a parser, an EMR variable type mapping table, or variable type manager) of FIG. 9 are described below to be included in the server 200, when the creation of a recognition model is performed by an external electronic device (e.g., a separate server) other than the server 200, the components (e.g., a parser, EMR variable type mapping table, or variable type manager) of FIG. 9 may be included in the external electronic device.

In operation 810, the server 200 may parse at least one piece of EMR data into at least one element (e.g., into one or more discrete elements). As an example, an example EMR 1000 which follows HL7 standards is described. The portion 1010 which indicates patient's name in the EMR 1000 may be included. For example, the patient's name "Chalmers" 1030, the patient's first name and middle name, "Peter" and "James" 1020 may be recorded in the patient's name portion 1010 of the EMR 1000. Referring to FIG. 9, the server 200 may parse "Chalmers" and "Peter James" of the EMR 910 using the parser 920 included in the server 200 and define "Chalmers" 1030 and "Peter James" 1020 as elements 931, 932, and 933, respectively.

In operation 820, the server 200 may store each piece of EMR data including each element associated with a number of corresponding variable types, by referencing an EMR variable type mapping table. Referring to FIG. 9, the variable type manager 940 included in the server 200 may associate each 931, 932, and 933 of elements 930 to a corresponding variable type by referencing the EMR variable type mapping table 950. Thereafter, the server 200 may store EMR data 960 including the elements 931, 932, and 933 and their corresponding variable types in, e.g., the memory 220. The EMR variable type mapping table 950 is a table that associates record type, record definition, and variable type. An example of part of the EMR variable type mapping table 950 is as follows.

TABLE 1

| Record type | Record definition | Variable type |
|---|---|---|
| Patient | Last name + first name and middle name | patient's name |
| medication prescription | administered medication | medication name |

In the first row of Table 1, record type may specify what the record is about, record definition may specify the format in which elements are recorded in variables, and record type may specify the type of variables. For example, since in the example shown in FIG. 10, the element of "Chalmers" 1030 is the last name, and the element of "Peter James" 1020 is the first name and middle name (or given name), the variable type "Patient's name" which is defined with "last name+ first name and middle name" may be configured. Referring to Table 1, the EMR data with a variable type 1040 of "Patient's name" and a record definition of "Chalmers"+ "Peter James" may have a record type of "Patient." Referring to FIG. 10 and the EMR variable type mapping table exemplified as Table 1, the elements "Peter James" 1020 and "Chalmers" 1030 may be combined together and be associated with the variable type "patient's name." At least one piece of EMR data 1050 may include elements associated with variable type.

In operation 830, the server 200 may apply machine learning at least one piece of stored EMR data 960 and 1050. According to an embodiment, as described above in connection with FIG. 6, the server 200 may create recognition models corresponding to divided user groups or disease names by executing machine learning on the EMR data 960 and 1050 limited in range by the divided user groups or disease names.

Figure 11:
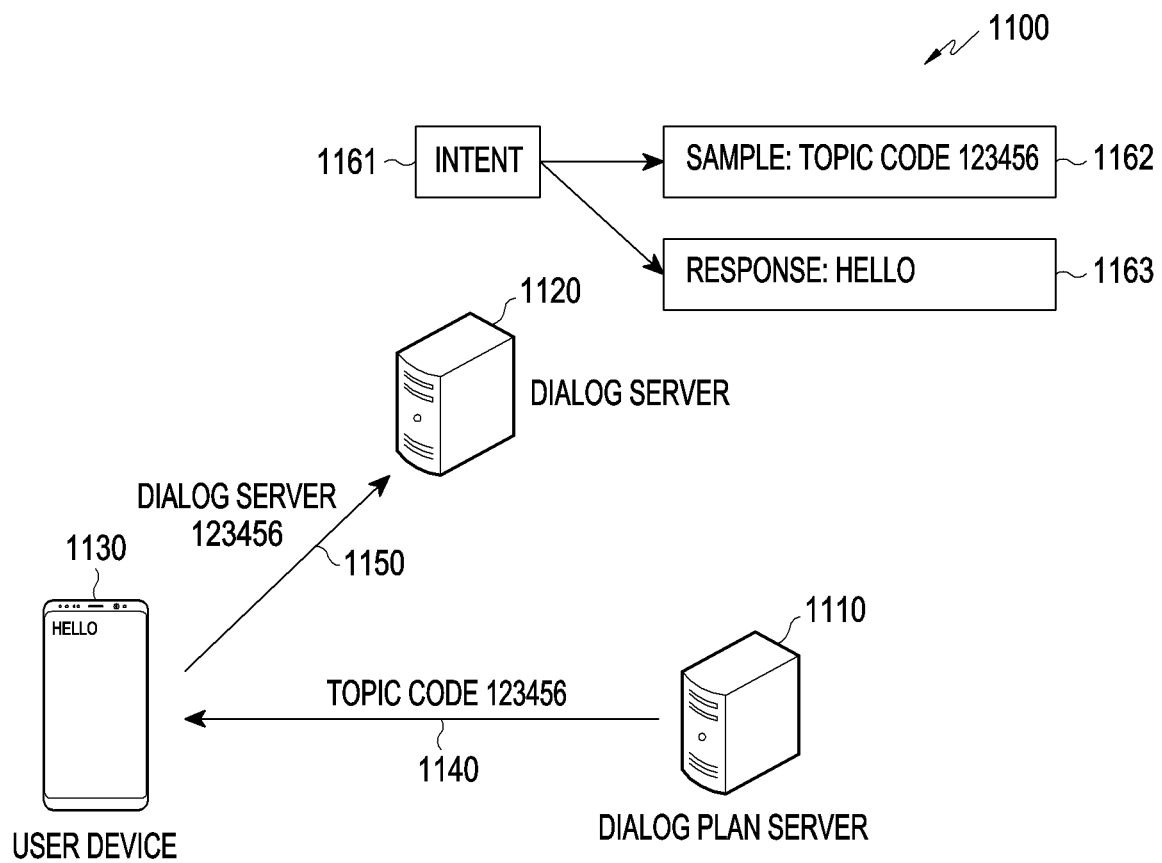
FIG. 11 is a view illustrating a process performed for a dialog service provider to start a dialog earlier than a user according to an example embodiment.

FIG. 11 is a view illustrating a process 1100 performed for a dialog service provider to start a dialog earlier than a user according to an embodiment. Referring to FIG. 11, there may be provided a dialog server 1120 (e.g., the server 200) and a dialog plan server 1110 for a user device 1130 (e.g., the electronic device 101) to provide a dialog service to the user. According to an embodiment, the dialog plan server 1110 may be a separate server from the dialog server 1120. According to an embodiment, the dialog plan server 1110 and the dialog server 1120 may be implemented as the same server (e.g., the server 200).

The dialog plan server 1110 may transmit (1140) topic code to the user device 1130. The topic of dialog may be limited corresponding to the topic code. For example, a particular topic code may correspond to identifying whether the user regularly takes the prescribed medication. As another example, the particular topic code may correspond to authentication as to whether the person currently using the application is the same person as the patient related to the logged-in account. The topic code may be determined based on EMR data related to the user. The user device 1130 may invoke the received topic code from the background and transmit (1150) it to the dialog server 1120. According to an embodiment, the user device 1130 may transmit (1150) a dialog start request containing the topic code to the dialog server 1120. According to an embodiment, the operation of transmitting (1150) the topic code or the operation of transmitting the dialog start request may not be output by the voice input/output device (e.g., the sound output device 155) of the user device 1130 or a display (e.g., the display device 160). In other words, the operation of transmitting (1150) the topic code or the operation of transmitting the dialog start request may not be known to the user. Receiving (1150) the topic code, the dialog server 1120 may identify the utterance which is to be provided to the user device 1130 based on the relationship between the intent 1161, the topic code 1162, and the response 1163. FIG. 11 illustrates an example in which the dialog server 1120 receives (1150) the topic code and determines that the response 1163 is "Hello" corresponding to topic code 123456 (1162). The dialog server 1120 may transmit utterance data corresponding to the determined utterance to the user device 1130. Receiving the utterance data from the dialog server 1120, the user device 1130 may output a voice or text or both a voice and text corresponding to the utterance data. FIG. 11 illustrates an example in which a bot, i.e., the dialog service provider, outputs the utterance "Hello" on the display of the user device 1130. Since the utterance of the bot, which is the dialog service provider, may be determined based on the topic code determined by the dialog plan server 1110, the bot's utterance may occur before the user's utterance is issued.

Meanwhile, in a case where the dialog server 1120 uses a dialog model, e.g., receive query-send response, unless an utterance is first received from the user, no response may be sent out and, thus, the dialog server 1120 may not first send out utterance data. According to an embodiment, the dialog server 1120 may receive the topic code as a query from the user device 1130 and send utterance data corresponding thereto. Thus, despite using the receive query-send response dialog model, the server 1120 may first send out utterance data. According to an embodiment, the dialog plan server 1110 and the dialog server 1120 may be implemented as a single server. In this case, the integrated server itself may be associated with the user account or may create an independent topic code from the user account, identify utterance data corresponding to the created topic code, and send out the utterance data to the user device 1130.

Figure 12:
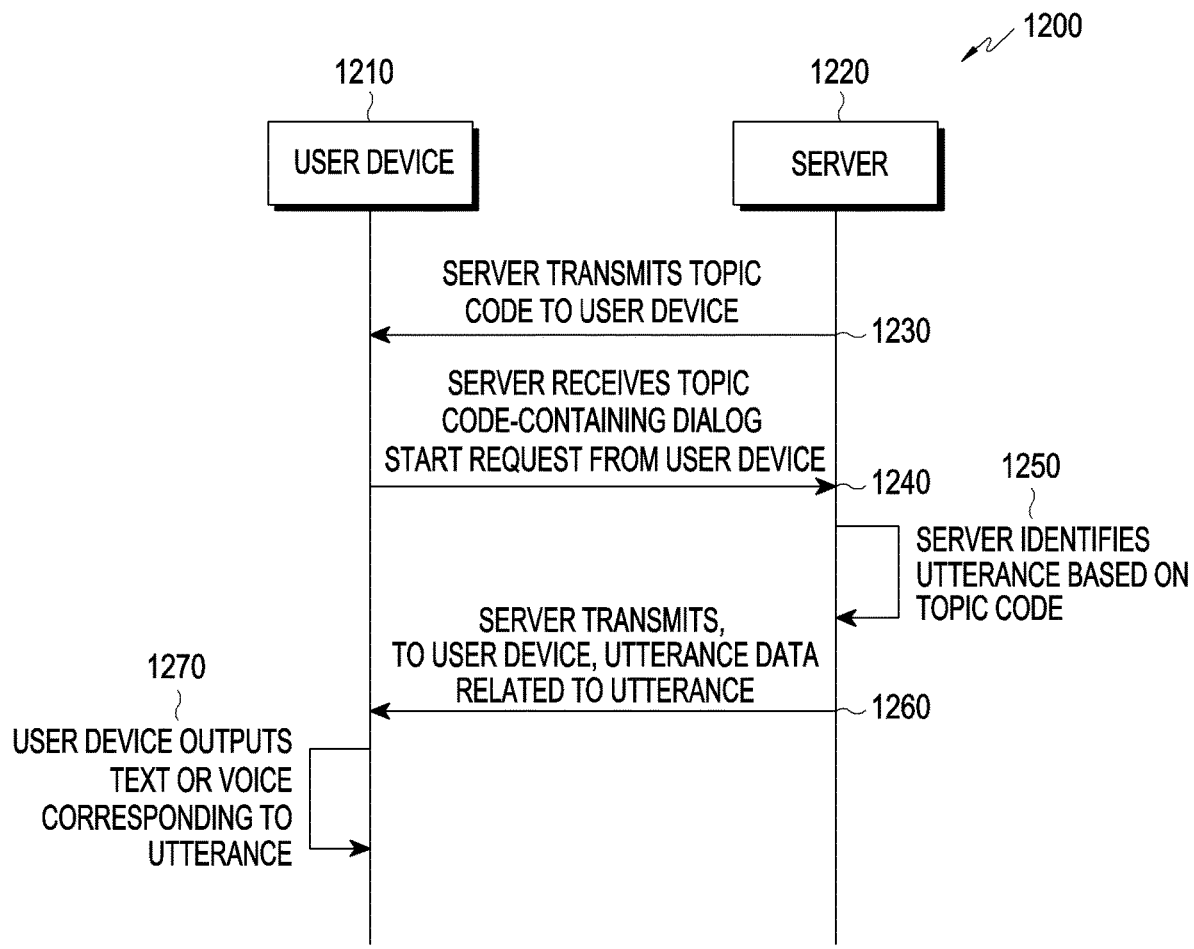
FIG. 12 is a view illustrating a process performed for a dialog service provider to start a dialog earlier than a user according to an example embodiment.

FIG. 12 is a view illustrating a process 1200 performed for a dialog service provider to start a dialog earlier than a user according to an embodiment. Specifically, FIG. 12 illustrates a process performed by a server 1220 and a user device 1210 (e.g., the electronic device 101) for a dialog service provider to start a dialog earlier than the user in a case where the dialog server 1120 and dialog plan server 1110 of FIG. 11 are implemented as the same server 1220 (e.g., the server 200).

In operation 1230, the server 1220 may transmit the topic code to the user device 1210. In operation 1240, the server 1220 may receive a dialog start request containing the topic code from the user device 1210. According to an embodiment, the topic code or the dialog start request may not be output by the voice input/output device (e.g., the sound output device 155) of the user device 1210 or a display (e.g., the display device 160). In operation 1250, the server 1220 may identify the utterance based on the topic code. Thereafter, in operation 1260, the server 1220 may transmit utterance data related to the utterance to the user device 1210. In operation 1270, the user device 1210 may output a voice corresponding to the utterance through the voice input/output device (e.g., the sound output device 155) based on the received utterance data and/or output a text corresponding to the utterance through a display (e.g., the display device 160).

Figure 13:
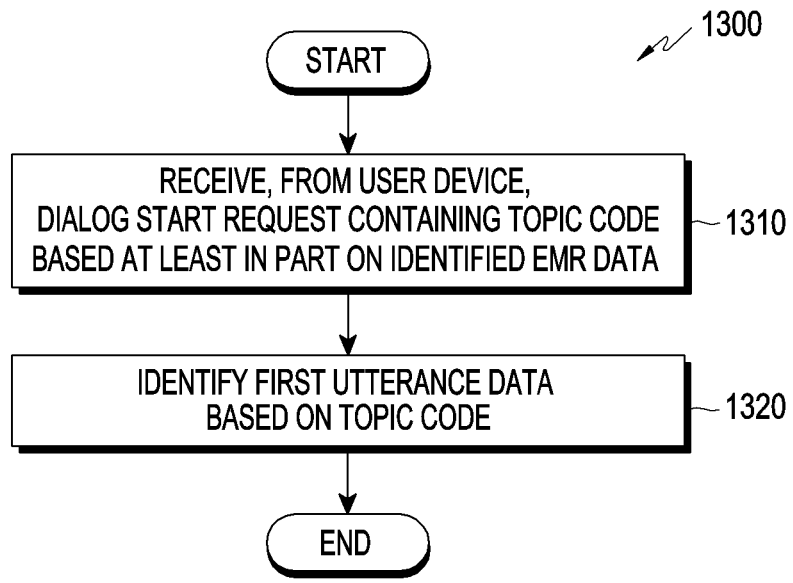
FIG. 13 is a flowchart illustrating a method performed on a server to start a dialog earlier than a user according to an example embodiment.

FIG. 13 is a flowchart illustrating a method 1300 performed on a server to start a dialog earlier than a user according to an embodiment. In operation 1310, a server (e.g., the server 200) may receive, from a user device (e.g., the electronic device 101), a dialog start request containing a topic code determined based at least in part on identified EMR data. The EMR data may be EMR data stored in association with a first user account identified to have been logged in on the user device. In operation 1320, the server 200 may identify first utterance data based on the received topic code.

Figure 14:
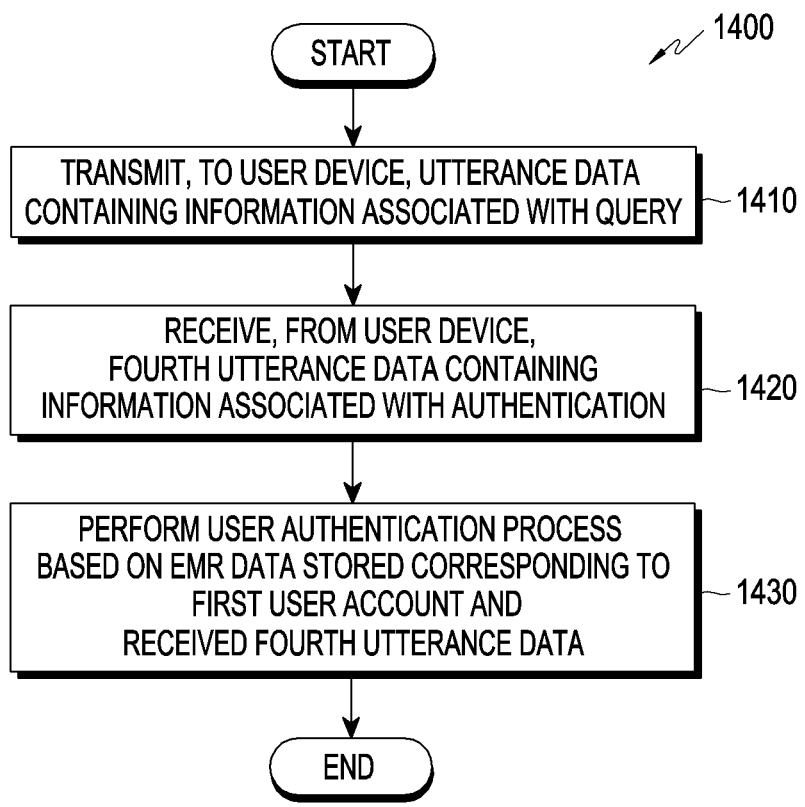
FIG. 14 is a flowchart illustrating an operation performed on a server to authenticate a user according to an example embodiment.

FIG. 14 is a flowchart illustrating an operation 1400 performed on a server to authenticate a user according to an embodiment. In operation 1410, a server (e.g., the server 200) may transmit, to a user device (e.g., the electronic device 101), utterance data containing information associated with query. The query may be a query for identifying whether the user currently using a dialog service is the same figure as the one specified by the user account. According to an embodiment, the query may regard personal information about a patient specified by the user account. For example, the query may be related to the patient's full name, family name, middle name, first name, maiden name, address, birth date, or age. According to an embodiment, the query may be related to the medical record of the patient specified by the user account. For example, the query may be related to the name of the patient's primary care doctor, the last time when he or she went to the hospital, the time when the patient got surgery, and details of the medication the patient takes, e.g., the fact that he or she takes yellow pills. According to an embodiment, the query may be related to information about the caregiver, e.g., the caregiver's name. Various examples of the query as proposed herein are not selective but rather compatible. For example, according to an embodiment, one query may be selected from a set of queries including all queries related to the patient's medical record and queries regarding the patient's personal information. Alternatively, one query may be selected from a set of queries including queries regarding the patient's personal information, queries related to the patient's medical record, and information regarding the caregiver.

In operation 1420, the server 200 may receive, from the user device, fourth utterance data including information associated with user authentication. The fourth utterance data may be related to a response to the query described above in connection with operation 1410 as the user entered to the user device.

In operation 1430, the server 200 may perform a user authentication process based on the EMR data stored corresponding to the first user account and the fourth utterance data received from the user device. According to an embodiment, the server may compare the user's response to the query which is derived based on the fourth utterance data with the patient's information related to the query which is derived based on the stored EMR data. Details of the user authentication process are described below.

Figure 15:
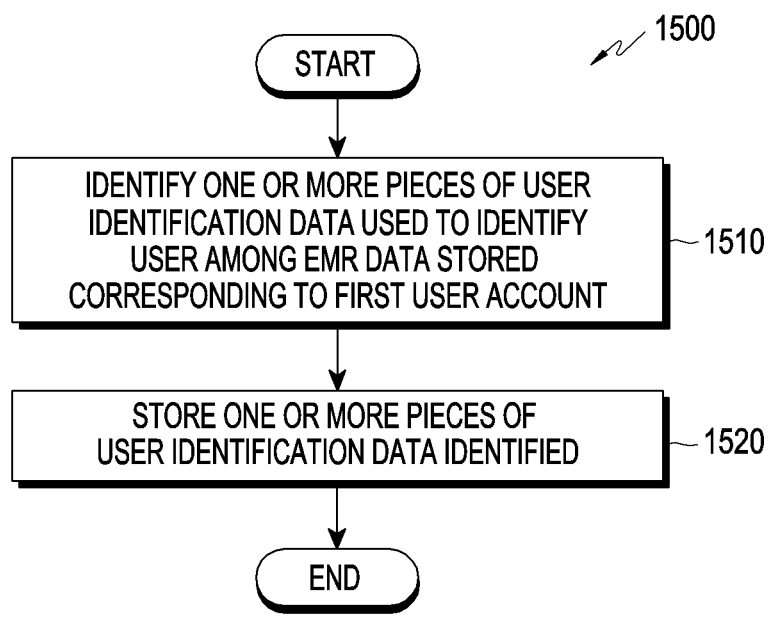
FIG. 15 is a flowchart illustrating an operation performed on a server to authenticate a user according to an example embodiment.

FIG. 15 is a flowchart illustrating an operation 1500 performed on a server to authenticate a user according to an embodiment. In operation 1510, the server 200 may identify one or more pieces of user identification data used to identify the user among EMR data stored corresponding to the first user account. As set forth above in connection with operation 320 of FIG. 3, the EMR data stored corresponding to the first user account may be stored in the server 200 or an external device (e.g., a separate server) other than the server 200. According to an embodiment, in a case where the EMR data stored corresponding to the first user account is stored in the external device other than the server 200, the server 200 may receive one or more pieces of user identification data used to identify the user from the external device, thereby identifying one or more pieces of user identification data. In operation 1520, the server 200 may store the one or more pieces of identified user identification data. According to an embodiment, in a case where the EMR data stored corresponding to the first user account is stored in the server 200, the server 200 may store the one or more pieces of user identification data in a separate directory distinguished from the other EMR data. Contents which may be contained in the user identification data may be the same as what has been described above in connection with the query and operation 1410 of FIG. 14. In other words, the user identification data may regard the patient's personal information specified by the user account. According to an embodiment, the user identification data may relate to the patient's medical record specified by the user account. According to an embodiment, the user identification data may relate to information regarding the caregiver, e.g., the caregiver's name. Various examples proposed herein regarding the user identification data may not be selective but may rather be compatible. For example, according to an embodiment, the user identification data may include both data regarding the patient's personal information and data related to the patient's medical record. According to an embodiment, the user identification data may include all of data regarding the patient's personal information, data related to the patient's medical record, and data regarding the caregiver.

Figure 16:
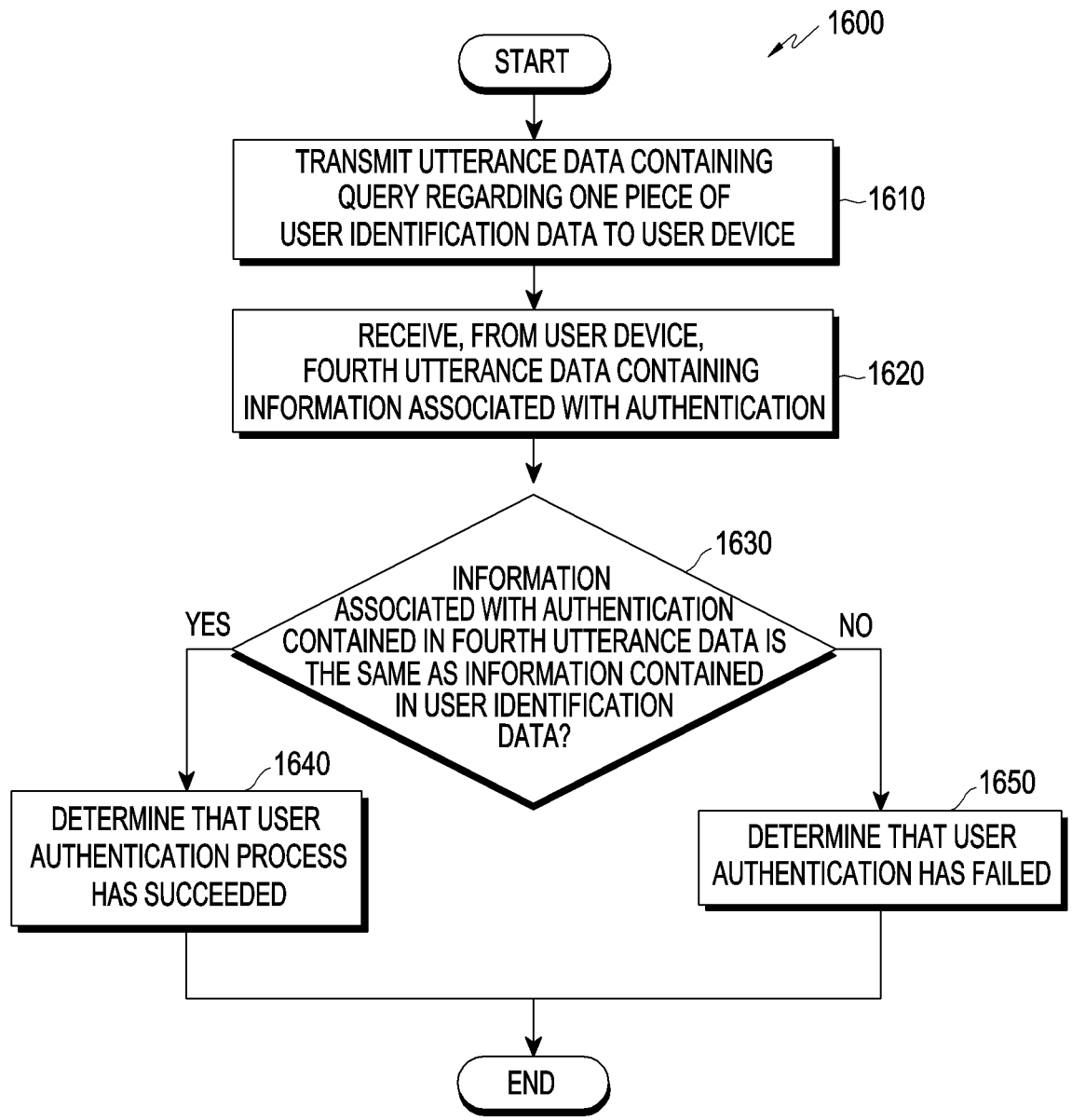
FIG. 16 is a flowchart illustrating an operation performed on a server to authenticate a user according to an example embodiment.

FIG. 16 is a flowchart illustrating an operation 1600 performed on a server to authenticate a user according to an embodiment. In operation 1610, the server 200 may transmit utterance data containing a query regarding one piece of user identification data to a user device (e.g., the electronic device 101). Details of the user identification data and query are the same as those described above in connection with operation 1410 of FIG. 14 and operation 1520 of FIG. 15 and no repetitive description is given below. The user device may receive the query-containing utterance data, output a voice corresponding to the utterance through the voice input/output device (e.g., the sound output device 155) based on the received utterance data, and/or output a text corresponding to the utterance through a display (e.g., the display device 160).

In operation 1620, the server 200 may receive fourth utterance data including information associated with user authentication from the user device. According to an embodiment, the fourth utterance data may relate to a response entered to the voice input/output device (e.g., the input device 150) of the user device as a response to the user's query.

In operation 1630, the server 200 may identify whether the information associated with user authentication contained in the fourth utterance data matches the information included in the query-related user identification data. According to an embodiment, the server 200 may compare the information associated with user authentication contained in the user's response to the query, which is derived based on the fourth utterance data, with the patient's information related to the query which is derived based on the stored user identification data. When the information associated with user authentication contained in the fourth utterance data matches the information contained in the query-related user identification data, the server 200 may determine that the user authentication process has succeeded in operation 1640.

If the information associated with user authentication contained in the fourth utterance data does not match the information contained in the query-related user identification data, the server 200 may determine that the user authentication process has failed in operation 1650. According to an embodiment, upon determining that user authentication has failed, the server 200 may determine that the user authentication process has failed. When the user authentication process is determined to have failed, the server 200 may notify the user device of the failure in the user authentication process and terminate the dialog service. According to an embodiment, in response to the failure in the user authentication process which has been known to the user device by the server 200, the user device may output a text and/or voice to guide an operation for reaching an organization which provides dialog services. According to an embodiment, when the user authentication is determined to have failed, the server 200 may perform password authentication which is described below in connection with FIG. 20.

According to an embodiment, the server 200 may perform user authentication considering the property (e.g., voice print) of the fourth utterance data as well as the content identified from the fourth utterance data. For example, although the content identified from the fourth utterance data is determined to be the same as information contained in the user identification data, if the voice print stored in association with the first user account is identified not to match the voice print of the fourth utterance data, the server 200 may determine that the user authentication has failed. The above-described voice print is merely an example, and it will readily be appreciated by one of ordinary skill in the art that any property which is identifiable from the fourth utterance data is available to an additional user authentication process.

According to an embodiment, the user authentication process may be performed immediately after the user responds to the first utterance of the dialog service provider. According to an embodiment, the user authentication process may be performed at each predetermined interval.

Figure 17:
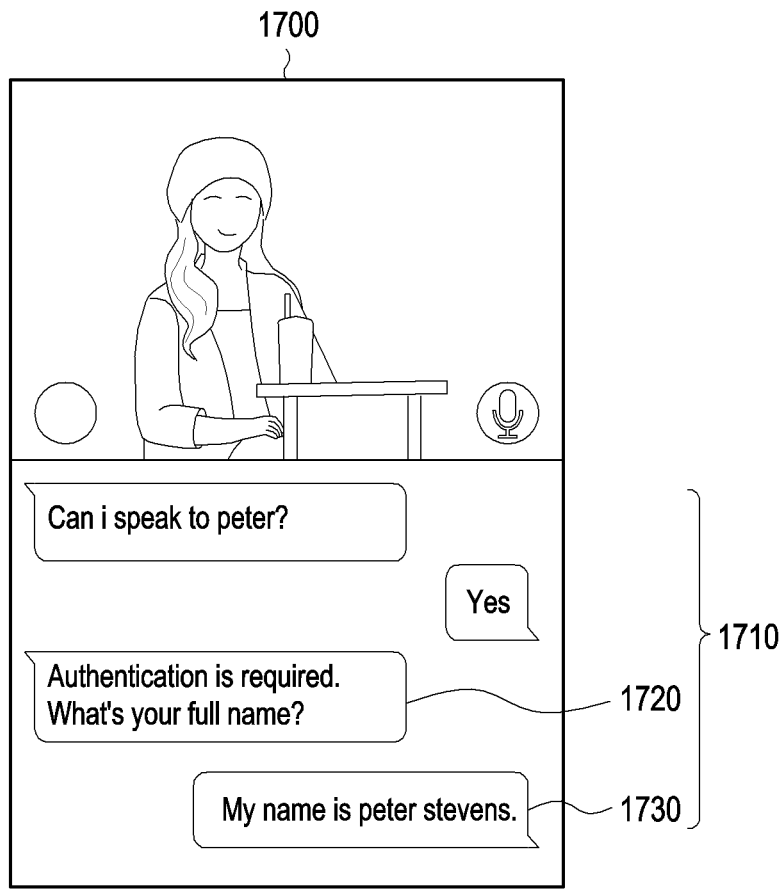
FIG. 17 is a view illustrating an example screen displayed on a user device when an authentication process proceeds according to an example embodiment.

FIG. 17 is a view illustrating an example screen 1700 displayed on a user device when a user authentication process proceeds according to an embodiment. Specifically, FIG. 17 illustrates an example service screen 1700 which may be displayed on a display (e.g., the display device 160) of a user device (e.g., the electronic device 101) when the server 200 performs operations 1610 and 1620 of FIG. 16. According to an embodiment, the service screen 1700 may include a dialog display area 1710. Details of the dialog display area 1710 are the same as the dialog display area 410 of FIG. 4 and no repetitive description is presented below. According to an embodiment, to perform a user authentication process, the dialog service provider may send a query regarding the full name which is example user identification data along with a message indicating that user authentication is needed (1720). The query may be displayed on the display of the user device in the form of a text or may be output in the form of a voice through a voice input/output device (e.g., the sound output device 155) of the user device as denoted by 1720. According to an embodiment, the user may then enter a response to the query through the voice input/output device (e.g., the input device 150) of the user device, and a text corresponding to the entered response may be displayed on the display of the user device (1730). In this case, the user may be aware how the response he or she entered is recognized by the user device. According to an embodiment, there may be no dialog display area 1710, no text corresponding to the utterance data may be output, and an utterance may be entered and output in the form of a voice via the user device's voice input/output device (e.g., the sound output device 155 and the input device 150).

Figure 18:
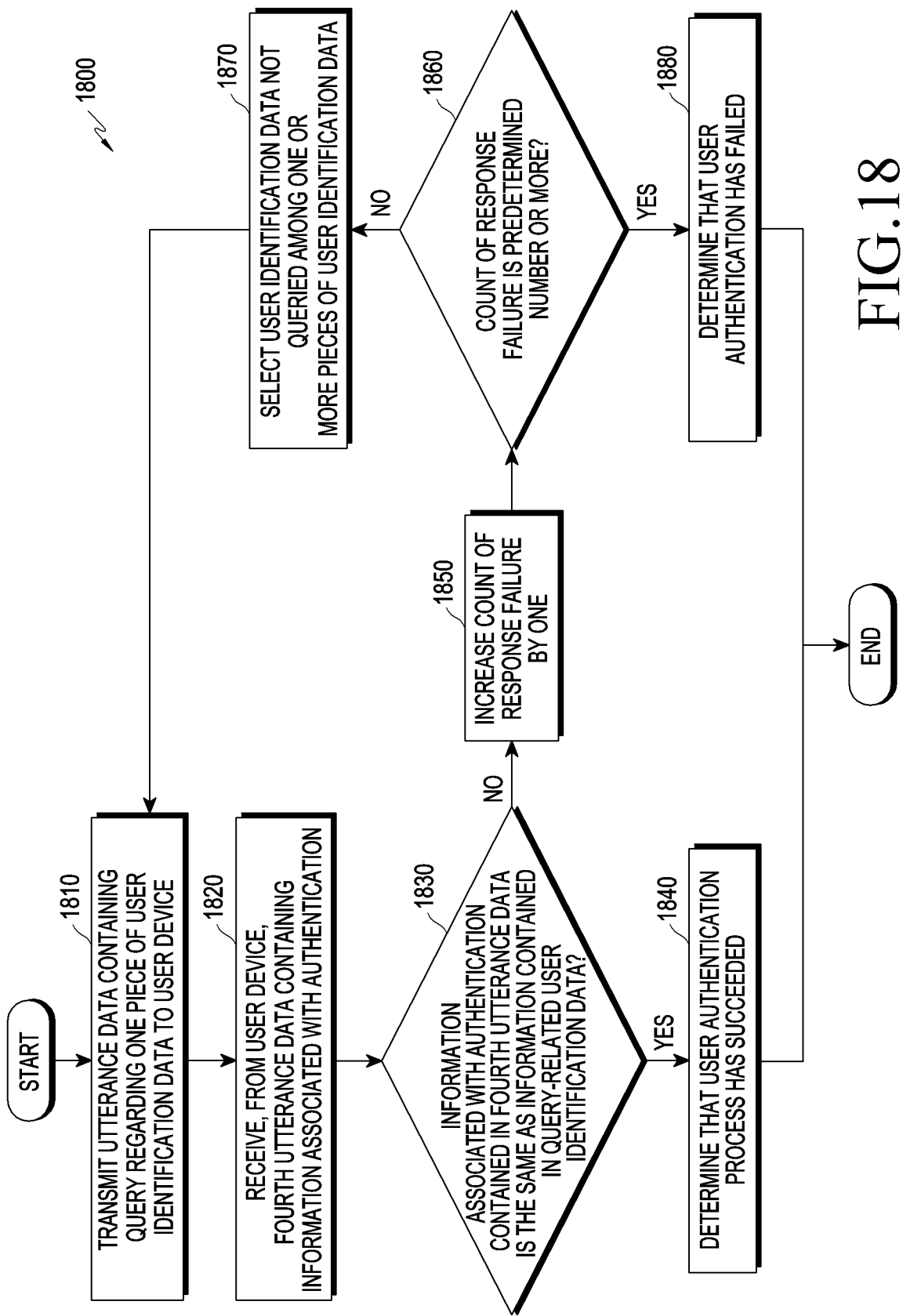
FIG. 18 is a flowchart illustrating an operation performed on a server to authenticate a user according to an example embodiment.

FIG. 18 is a flowchart illustrating an operation 1800 performed on a server to authenticate a user according to an embodiment. In operation 1810, the server 200 may transmit utterance data containing a query regarding one piece of user identification data to a user device (e.g., the electronic device 101). In operation 1820, the server 200 may receive fourth utterance data including information associated with user authentication from the user device. In operation 1830, the server 200 may identify whether the information associated with user authentication contained in the fourth utterance data matches the information included in the query-related user identification data. When the information associated with user authentication contained in the fourth utterance data matches the information contained in the query-related user identification data, the server 200 may determine that the user authentication process has succeeded in operation 1840. Details of operations 1810 to 1840 are the same as operations 1610 to 1640 of FIG. 16 and no repetitive description is presented below.

If the information associated with user authentication contained in the fourth utterance data does not match the information contained in the query-related user identification data, the server 200 may increase the count of response failure by one. Thereafter, in operation 1860, the server 200 may identify whether the count of response failure is a predetermined number or more. When the count of response failure is less than the predetermined number, the server 200 may select user identification data which was not subjected to query among one or more pieces of user identification data in operation 1870. Thereafter, the server 200 goes to operation 1810, sending the user device utterance data containing a query regarding newly selected user identification data which differs from the first user identification data. When the count of response failure is the predetermined number or more, the server 200 may determine that user authentication has failed in operation 1880. Operations after the server 200 determines that user authentication has failed are the same as those described above in connection with operation 1650 of FIG. 16 and no repetitive description is given below. As compared with the method shown in FIG. 16, the operation 1800 of FIG. 18 may allow as many inconsistent responses as (a predetermined count (number) of response failures−1).

Figure 19:
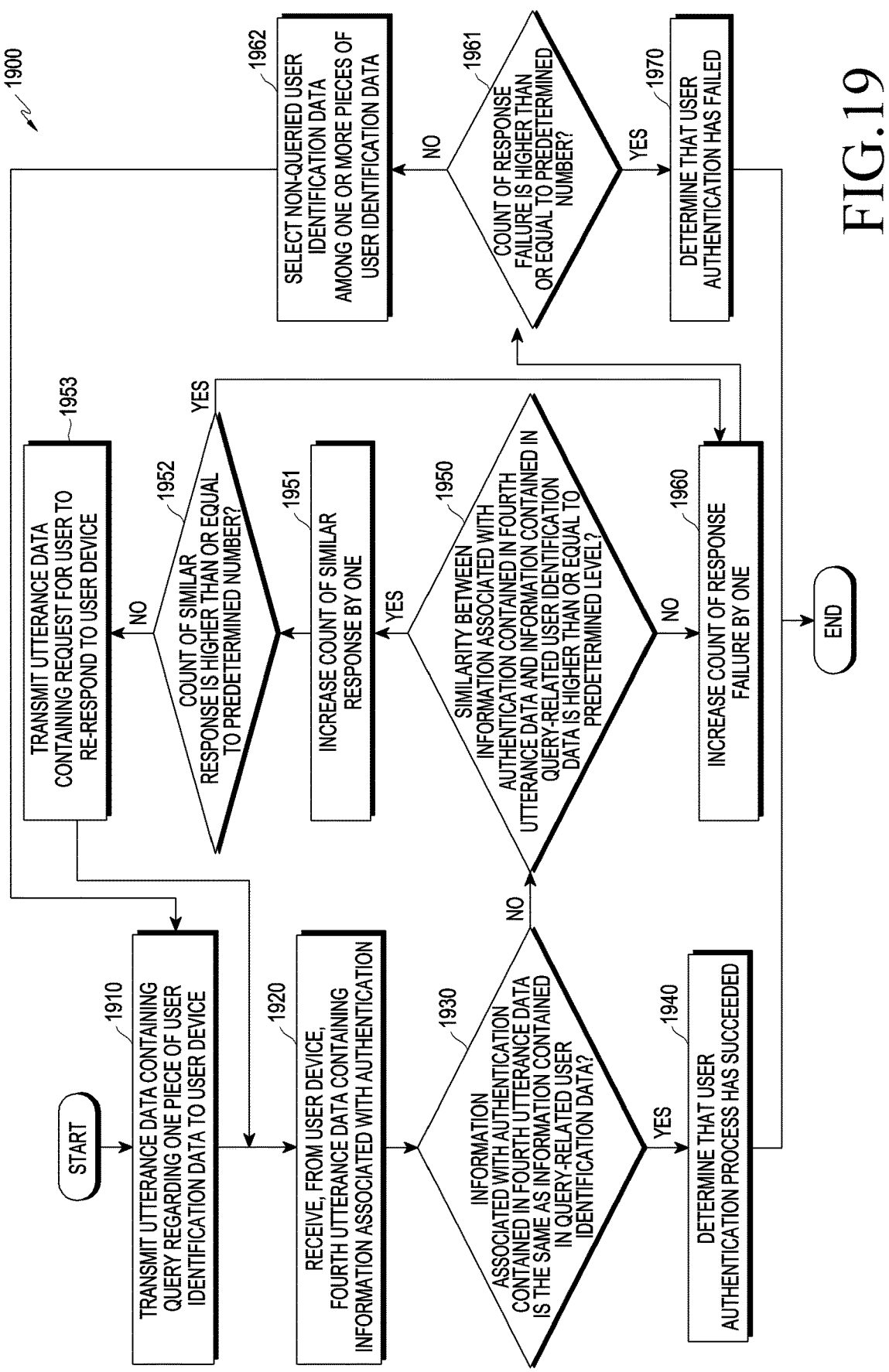
FIG. 19 is a flowchart illustrating an operation performed on a server to authenticate a user according to an example embodiment.

FIG. 19 is a flowchart illustrating an operation 1900 performed on a server to authenticate a user according to an embodiment. In operation 1910, the server 200 may transmit utterance data containing a query regarding one piece of user identification data to a user device (e.g., the electronic device 101). In operation 1920, the server 200 may receive fourth utterance data including information associated with user authentication from the user device. In operation 1930, the server 200 may identify whether the information associated with user authentication contained in the received fourth utterance data matches the information included in the query-related user identification data. When the information associated with user authentication contained in the fourth utterance data matches the information contained in the query-related user identification data, the server 200 may determine that the user authentication process has succeeded in operation 1940. Details of operations 1910 to 1940 are the same as operations 1610 to 1640 of FIG. 16 and no repetitive description is presented below.

If the information associated with user authentication contained in the fourth utterance data does not match the information contained in the query-related user identification data, the server 200 may, in operation 1950, identify whether the similarity between the information associated with user authentication contained in the fourth utterance data and the information contained in the query-related user identification data is higher than or equal to a predetermined level. As described above in connection with operation 340 of FIG. 3, the fourth utterance data may be data indicating a voice signal, data indicating a text-type natural language obtained by performing an STT process on a voice signal, or data obtained by a natural language understanding (NLU) on a text-type natural language. According to an embodiment, when the fourth utterance data is data indicating a voice signal, an STT and NLU process may be performed on a voice signal received by the server 200. Generally, as obtained by performing an STT and NLU process on a voice signal by the server 200, a plurality of results, rather than a single result, may be associated with probability or accuracy and may be listed up. The server 200 may determine that the result with the highest probability or accuracy among the plurality of results listed-up is the information associated with user authentication contained in the fourth utterance data. Unless the result with the highest probability or accuracy as determined to be the information associated with user authentication contained in the fourth utterance data matches the information contained in the query-related user identification data, the server 200 may determine whether there is a result matching the information contained in the query-related user identification data among the other multiple results listed-up and whether the probability or accuracy of the matching result is a predetermined level or more. In such a case, the server 200 may identify that the similarity between the information associated with user authentication contained in the fourth utterance data and the information contained in the query-related user identification data is the predetermined level or more. According to an embodiment, when the fourth utterance data is data indicating a text-type natural language obtained by performing an STT process on a voice signal or data obtained by performing a natural language understanding (NLU) process on a text-type natural language, the server 200 may receive, as the fourth utterance data, the plurality of results listed-up in association with the probability or accuracy which is the result of the STT process and/or NLU process from the user device. Unless the result with the highest probability or accuracy as determined to be the information associated with user authentication contained in the fourth utterance data matches the information contained in the query-related user identification data, the server 200 may determine whether there is a result matching the information contained in the query-related user identification data among the other multiple results listed-up and whether the probability or accuracy of the matching result is a predetermined level or more, thereby determining whether the similarity between the pieces of information contained in the query-related user identification data is a predetermined level or more.

When the similarity between the pieces of information contained in the query-related user identification data is the predetermined level or more, the server 200 may increase the count of similar response by one in operation 1951. In operation 1952, the server 200 may identify whether the count of similar response is higher than or equal to a predetermined number. When the count of similar response is less than the predetermined number, the server 200 may transmit utterance data containing a request to re-respond to the user to the user device in operation 1953. When the count of similar response is the predetermined number or more, the server 200 may increase the count of response failure by one in operation 1960.

Upon identifying that the similarity between the information associated with user authentication contained in the fourth utterance data and the information contained in the query-related user identification data is lower than the predetermined level in operation 1950, the server 200 may increase the count of response failure by one in operation 1960.

After performing operation 1960, the server 200 may identify whether the count of response failure is higher than or equal to the predetermined number in operation 1961. When the count of response failure is smaller than the predetermined number, the server 200 may select user identification data which was not subjected to query among one or more pieces of user identification data in operation 1962. When the count of response failure is higher than or equal to the predetermined number, the server 200 may determine that user authentication has failed in operation 1970. Details of operations 1960, 1961, 1962, and 1970 are the same as operations 1850, 1860, 1870, and 1880 of FIG. 18 and no repetitive description is presented below. As compared with the method shown in FIGS. 16 and 18, the operation 1900 of FIG. 19 may allow as many inconsistent, but similar, responses as (a predetermined count of similar response-1). Although FIG. 19 illustrates an example of adding a response-allowing feature similar to the operation 1800 of FIG. 18, an embodiment of adding a response-allowing feature similar to the method of FIG. 16 is possible as well. In this case, although incorrect responses with a similarity of a predetermined level or less with reference to the correct response are not allowed, incorrect responses with a similarity of the predetermined level or more with reference to the correct response may be allowed to some degree.

Figure 20:
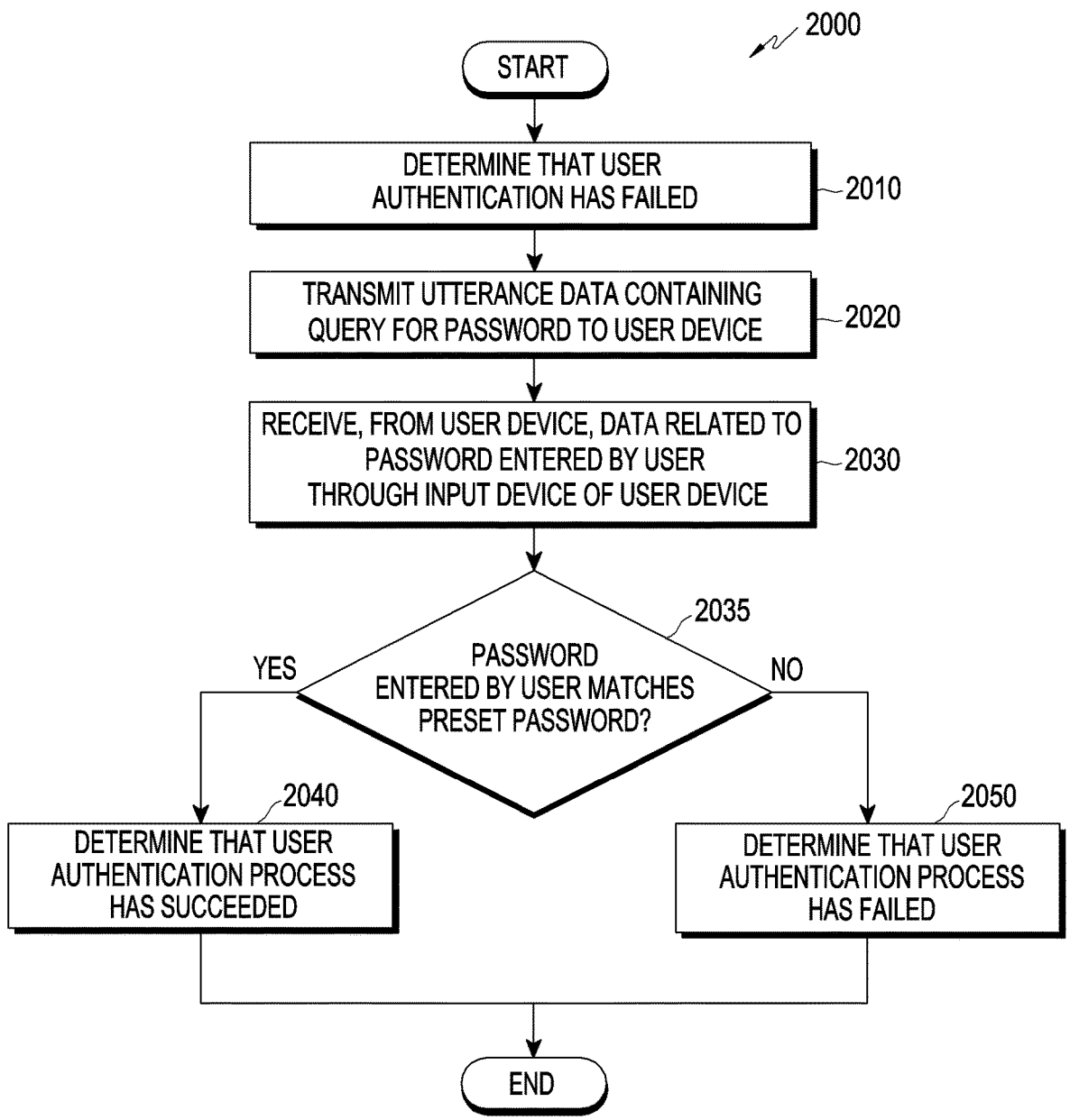
FIG. 20 is a flowchart illustrating an operation performed on a server to authenticate a user according to an example embodiment.

FIG. 20 is a flowchart illustrating an operation 2000 performed on a server to authenticate a user according to an embodiment. Specifically, FIG. 20 illustrates a password authentication process performed after user authentication is determined to have failed. In operation 2010, the server 200 may determine that user authentication has failed. Various scenario cases in which the server 200 may determine that user authentication has failed have been described above in connection with FIGS. 16, 18, and 19 and no repetitive description is given below. In operation 2020, the server 200 may transmit utterance data containing a query for a password to a user device (e.g., the electronic device 101). The user device may output a voice corresponding to the utterance through the voice input/output device (e.g., the sound output device 155) based on the received utterance data, and/or output a text corresponding to the utterance through a display (e.g., the display device 160).

In operation 2030, the server 200 may receive, from the user device, data related to the password entered by the user through the input device 150 of the user device. The input device 150 of the user device may be an input device, e.g., a mouse, touch pad, or keyboard other than the voice input/output device. In operation 2035, the server 200 may identify whether the password entered by the user matches a preset password. When the password entered by the user matches the preset password, the server 200 may determine that the user authentication process has succeeded in operation 2040. Unless the password entered by the user matches the preset password, the server 200 may determine that the user authentication process has failed in operation 2050. Details of determining that the user authentication process has failed by the server 200 are the same as those described above in connection with operation 1650 of FIG. 16 and no repetitive description is presented below.

According to an embodiment, similar to what is shown in FIG. 18, the password authentication method of FIG. 20, rather than immediately determining that the authentication process has failed when the passwords mismatch, may increase the count of response failure by one and, when the count of response failure is less than the predetermined number, re-receive a password from the user to thereby permit entry of an incorrect response (predetermined number-1). According to an embodiment, EMR data may contain the patient's fingerprint data. In this case, the server 200 may receive fingerprint information, instead of password, through a fingerprint recognition sensor of the user device and compare the received fingerprint information with the patient's fingerprint data, thereby performing user authentication on the patient. According to an embodiment, user authentication may be performed on the patient using pattern entry rather than password. According to an embodiment, user authentication may be performed using the user's EMR profile instead of password authentication. In this case, the server 200 may transmit utterance data containing a query regarding the user's EMR profile to a user device (e.g., the electronic device 101) in operation 2020, receive, from the user device, data related to a response to the query regarding the EMR profile entered by the user through the input device of the user device in operation 2030, and identify whether the response to the query regarding the EMR profile matches the EMR profile in operation 2035.

According to an embodiment, a server 200 configured to provide a dialog service includes a communication interface 230 configured to communicate with at least one user device, at least one processor 210 operatively connected with the communication interface 230, and a memory 220 operatively connected with the processor and configured to store at least one piece of electronic medical record (EMR) data, in which the memory 220 stores instructions executed to enable the processor 210 to identify login to a first user account by the user device using the communication interface 230, identify the EMR data stored in the memory 220 corresponding to the first user account based on at least part of a result of the identified login, identify first utterance data for utterance through the user device based on at least part of the identified EMR data before data associated with utterance is received from the user device using the communication interface 230, and transmit the first utterance data to the user device using the communication interface 230.

According to an embodiment, the instructions enable the processor 210 to receive second utterance data from the user device using the communication interface 230, obtain a result of recognizing the second utterance data by applying a recognition model to the received second utterance data, and transmit third utterance data identified based on at least part of the result of recognizing the second utterance data to the user device using the communication interface 230.

According to an embodiment, the recognition model may be obtained by applying machine learning to at least one piece of EMR data including the EMR data stored in the memory 220 corresponding to the first user account.

According to an embodiment, the instructions enable the processor 210 to identify the recognition model corresponding to the first user account among a plurality of recognition models previously stored in the memory 220.

According to an embodiment, when the at least one piece of EMR data is partially updated, the recognition model may be obtained by "learning" (e.g., applying machine learning on) the at least one piece of EMR data updated.

According to an embodiment, the learning of the at least one piece of EMR data may be performed by parsing the at least one piece of EMR data into at least one element, storing, in the memory 220, the at least one piece of EMR data including each of the at least one elements associated with a corresponding variable type by referring to an EMR variable type mapping table based on at least part of a result of the parsing, and learning the at least one piece of EMR data stored.

According to an embodiment, the instructions enable the processor 210 to receive a dialog start request including a topic code determined based on at least part of the identified EMR data from the user device using the communication interface 230, in which the user device is configured to receive the topic code from at least one of the server 200 or an external electronic device before a user enters a utterance and to refrain from outputting, via a voice output device of the user device or a display of the user device, information associated with the dialog start request or the topic code, and identify the first utterance data based on at least part of the topic code.

According to an embodiment, the instructions enable the processor 210 to receive fourth utterance data including information associated with user authentication from the user device using the communication interface 230 and perform a user authentication process based on at least part of the EMR data stored in the memory 220 corresponding to the first user account and the received fourth utterance data.

According to an embodiment, the user authentication process may be performed based on at least part of user identification data of the EMR data stored in the memory 220 corresponding to the first user account. The instructions enable the processor 210 to include information associated with a query for obtaining the fourth utterance data from the user device in the first utterance data or additional utterance data and transmit the information to the user device using the communication interface 230.

According to an embodiment, a method of operating a server 200 configured to provide a dialog service includes identifying login to a first user account by a user device using a communication interface 230, identifying EMR data stored in a memory 220 corresponding to the first user account based on at least part of a result of the identified login, identifying first utterance data for utterance through the user device based on at least part of the identified EMR data before data associated with utterance is received from the user device using the communication interface 230, and transmitting the first utterance data to the user device using the communication interface 230.

According to an embodiment, the method may further include receiving second utterance data from the user device using the communication interface 230, obtaining a result of recognizing the second utterance data by applying a recognition model to the received second utterance data, and transmitting third utterance data identified based on at least part of the result of recognizing the second utterance data to the user device using the communication interface 230.

According to an embodiment, the recognition model may be obtained by learning at least one piece of EMR data including the EMR data stored in the memory 220 corresponding to the first user account.

According to an embodiment, the method may further include identifying the recognition model corresponding to the first user account among a plurality of recognition models previously stored in the memory 220.

According to an embodiment, when the at least one piece of EMR data is partially updated, the recognition model may be obtained by learning the at least one piece of EMR data updated.

According to an embodiment, the learning of the at least one piece of EMR data may be performed by parsing the at least one piece of EMR data into at least one element, storing, in the memory 220, the at least one piece of EMR data including each of the at least one elements associated with a corresponding variable type by referring to an EMR variable type mapping table based on at least part of a result of the parsing, and learning the at least one piece of EMR data stored.

According to an embodiment, identifying the first utterance data may include receiving a dialog start request including a topic code determined based on at least part of the identified EMR data from the user device using the communication interface, in which the user device is configured to receive the topic code from at least one of the server or an external electronic device before a user enters a utterance and to refrain from outputting, via a voice output device of the user device or a display of the user device, information associated with the dialog start request or the topic code, and identifying the first utterance data based on at least part of the topic code.

According to an embodiment, the method may include receiving fourth utterance data including information associated with user authentication from the user device using the communication interface 230 and performing a user authentication process based on at least part of the EMR data stored in the memory 220 corresponding to the first user account and the received fourth utterance data.

According to an embodiment, the user authentication process may be performed based on at least part of user identification data of the EMR data stored in the memory corresponding to the first user account. Performing the user authentication process may include including information associated with a query for obtaining the fourth utterance data from the user device in the first utterance data or additional utterance data and transmitting the information to the user device using the communication interface 230.

According to an embodiment, an electronic device 101 configured to provide a dialog service may include a housing, a touchscreen display 160 exposed through a first portion of the housing, a communication interface 190 positioned inside the housing and configured to communicate with at least one external electronic device, a voice input/output device 150 and 155 disposed in a second portion and/or a third portion of the housing and configured to input and output a user's utterance data, a processor 120 positioned inside the housing and operatively connected with the display 160, the communication interface 190, and the voice input/output device 150 and 155, and a memory 130 positioned inside the housing and operatively connected with the processor 120, in which the memory 130 may store instructions executed to enable the processor 120 to transmit a request for login to a first user account using the communication interface 190, receive first utterance data identified based on at least part of EMR data stored corresponding to the first user account from the external electronic device using the communication interface 190 based on at least part of a result of the request, output at least one of a voice and a screen based on the first utterance data through at least one of the voice input/output device 150 and 155 and the display, and receive, from a user of the electronic device, the user's response to at least one of the output voice and screen through the voice input/output device 150 and 155.

According to an embodiment, the instructions enable the processor 120 to transmit second utterance data to the external electronic device using the communication interface 190 and receive, from the external electronic device using the communication interface 190, third utterance data identified based on at least part of a result of recognition obtained by applying a recognition model to the second utterance data.

According to an embodiment, the recognition model may be obtained by learning at least one piece of EMR data including the stored EMR data corresponding to the first user account.

According to an embodiment, the recognition model may be a recognition model identified as corresponding to the first user account among a plurality of pre-stored recognition models.

According to an embodiment, when the at least one piece of EMR data is partially updated, the recognition model may be obtained by learning the at least one piece of EMR data updated.

According to an embodiment, the learning of the at least one piece of EMR data may be performed by parsing the at least one piece of EMR data into at least one element, storing the at least one piece of EMR data including each of the at least one elements associated with a corresponding variable type by referring to an EMR variable type mapping table, and learning the at least one piece of EMR data stored.

According to an embodiment, the instructions enable the processor 120 to receive a topic code determined based on at least part of the stored EMR data using the communication interface 190 before entry of the user's utterance, transmit a dialog start request including the topic code using the communication interface 190, in which the electronic device 101 is configured to refrain from outputting information associated with the topic code or the dialog start request through the voice input/output device 150 and 155 or the display 160, and receive the first utterance data identified based on the topic code using the communication interface 190.

According to an embodiment, the instructions enable the processor 120 to receive the first utterance data or third utterance data including information about a query related to an authentication process based on the EMR data stored corresponding to the first user account using the communication interface 190, output at least one of a voice and a screen based on the first utterance data or the third utterance data using at least one of the voice input/output device 150 and 155 and the display 160, and transmit fourth utterance data related to the user's response to the query using the communication interface 190.

The electronic device according to certain embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that certain embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Certain embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to certain embodiments of the disclosure may be included and provided in a computer program product. The computer program products may be traded as commodities between sellers and buyers. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to certain embodiments, each component (e.g., a module or a program) of the above-described components may include a single entity or multiple entities. According to certain embodiments, one or more of the above-described components may be omitted, or one or more other components may be added. Alternatively or additionally, a plurality of components (e.g., modules or programs) may be integrated into a single component. In such a case, according to certain embodiments, the integrated component may still perform one or more functions of each of the plurality of components in the same or similar manner as they are performed by a corresponding one of the plurality of components before the integration. According to certain embodiments, operations performed by the module, the program, or another component may be carried out sequentially, in parallel, repeatedly, or heuristically, or one or more of the operations may be executed in a different order or omitted, or one or more other operations may be added.

As is apparent from the foregoing description, according to certain embodiments, there may be provided an electronic device of providing a dialog service based on an electronic medical record (EMR) and a method for providing a dialog service based on an EMR. Thus, the dialog service-provider electronic device may start a dialog earlier than the user and takes the lead in determining the topic of dialog. Since the electronic device leads the dialog, the electronic device may lead the user to efficiently complete tasks. Further, since the topic of a dialog is determined by the electronic device, the recognition rate of the user's utterance may be elevated within the range of the determined topic. The electronic device may perform a user authentication process to identify whether the user currently using a dialog service is the same figure as the one specified by the user account, thereby preventing leakage of the user's medical information to others.

What is claimed is:

1. A server for providing a dialog service, comprising:
   a communication interface configured to communicate with at least one user device;
   at least one processor operatively connected with the communication interface; and
   a memory operatively connected with the processor and configured to store electronic medical record (EMR) data,
   wherein the memory stores instructions that, when executed, cause the at least one processor to:
      identify that a login to a first user account is performed by a user device through the communication interface;
      in response to identifying the login to the first user account, identify stored EMR data corresponding to the first user account;
      determine a topic code based on the identified EMR data, before receiving data associated with utterance from the user device;
      transmit the topic code to the user device through the communication interface;
      receive a dialog start request including the topic code from the user device using the communication interface;
      in response to receiving the dialog start request, generate, based on the identified EMR data, first utterance data to be outputted through the user device; and
      transmit the generated first utterance data to the user device through the communication interface.

2. The server of claim 1, wherein the instructions further cause the at least one processor to:
   receive second utterance data from the user device through the communication interface;
   apply the received second utterance data to a recognition model to determine a corresponding function for execution; and
   transmit, to the user device using the communication interface, third utterance data generated based on executing the corresponding function.

3. The server of claim 2, wherein the recognition model is generated by executing machine learning on at least one piece of EMR data corresponding to the first user account.

4. The server of claim 3, wherein the instructions are further executable by the at least one processor to: identify the recognition model corresponding to the first user account from among a plurality of recognition models stored in the memory.

5. The server of claim 3, wherein the recognition model is generated by executing machine learning when the at least one piece of EMR data is updated.

6. The server of claim 3, wherein executing the machine learning on the at least one piece of EMR data includes:
   parsing the at least one piece of EMR data into one or more discrete elements,
   storing, in the memory, the at least one piece of EMR data including each of the one or more discrete elements, each associated with a variable type based on an EMR variable type mapping table, and
   executing the machine learning on the stored at least one piece of EMR data.

7. The server of claim 1, wherein:
   information associated with the dialog start request or the topic code is restricted from output via a speaker or a display of the user device.

8. The server of claim 1, wherein the instructions are executable by the at least one processor to:

receive, through the communication interface, a fourth utterance data including information associated with authentication from the user device; and execute authentication based on the EMR data stored in the memory that corresponds to the first user account, and the received fourth utterance data.

9. The server of claim 8, wherein the authentication is executed based on user identification data included in the EMR data, and wherein the instructions are further executable by the at least one processor to:

insert information associated with a query for obtaining the fourth utterance data from the user device within the first utterance data or additional utterance data, and transmit the included information to the user device using the communication interface.

10. A method for providing a dialog service in a server, the method comprising:

identifying that detecting a login to a first user account is performed by a user device through a communication interface of the server;

in response to identifying the login to the first user account, identifying electronic medical record (EMR) data corresponding to the first user account and stored in a memory of the server;

determining a topic code based on the identified EMR data, before receiving data associated with utterance from the user device;

transmitting the topic code to the user device through the communication interface;

receiving a dialog start request including the topic code from the user device using the communication interface;

in response to receiving the dialog start request, generating, based on the identified EMR data, first utterance data to be outputted through the user device; and transmitting the generated first utterance data to the user device through the communication interface.

11. The method of claim 10, further comprising:

receiving second utterance data from the user device through the communication interface;

applying the received second utterance data to a recognition model to determine a corresponding function for execution; and transmitting, to the user device using the communication interface, third utterance data generated based on executing the corresponding function.

12. The method of claim 11, wherein the recognition model is generated by executing machine learning on at least one piece of EMR data corresponding to the first user account.

13. The method of claim 12, further comprising identifying the recognition model corresponding to the first user account from among a plurality of recognition models stored in the memory.

14. The method of claim 12, wherein the recognition model is generated by executing machine learning when the at least one piece of EMR data is updated.

15. The method of claim 12, wherein executing the machine learning on the at least one piece of EMR data includes: parsing the at least one piece of EMR data into one or more discrete elements, storing, in the memory, the at least one piece of EMR data including each of the one or more discrete elements, each associated with a variable type based on an EMR variable type mapping table, and executing the machine learning on the stored at least one piece of EMR data.

16. The method of claim 10, wherein information associated with the dialog start request or the topic code is restricted from output via a speaker or a display of the user device.

17. The method of claim 10, further comprising:

receiving, through the communication interface, a fourth utterance data including information associated with authentication from the user device;

executing authentication based on the EMR data stored in the memory that corresponds to the first user account, and the received fourth utterance data;

inserting information associated with a query for obtaining the fourth utterance data from the user device within the first utterance data or additional utterance data; and transmitting the included information to the user device using the communication interface, wherein the authentication is executed based on user identification data included in the EMR data.

* * * * *